United States Patent
Zon et al.

(10) Patent No.: US 9,056,085 B2
(45) Date of Patent: Jun. 16, 2015

(54) METHODS FOR ENHANCING HEMATOPOIETIC STEM/PROGENITOR CELL ENGRAFTMENT

(75) Inventors: Leonard I. Zon, Wellesley, MA (US); Pulin Li, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 502 days.

(21) Appl. No.: 13/147,703

(22) PCT Filed: Feb. 3, 2010

(86) PCT No.: PCT/US2010/022992
§ 371 (c)(1),
(2), (4) Date: Sep. 1, 2011

(87) PCT Pub. No.: WO2010/096264
PCT Pub. Date: Aug. 26, 2010

(65) Prior Publication Data
US 2011/0305676 A1 Dec. 15, 2011

Related U.S. Application Data

(60) Provisional application No. 61/149,499, filed on Feb. 3, 2009, provisional application No. 61/189,929, filed on Jun. 15, 2009, provisional application No. 61/223,790, filed on Jul. 8, 2009.

(51) Int. Cl.
| | | |
|---|---|---|
| A61K 35/14 | (2006.01) | |
| A61K 31/196 | (2006.01) | |
| A61K 31/192 | (2006.01) | |
| A61K 35/12 | (2015.01) | |

(52) U.S. Cl.
CPC ......... *A61K 31/196* (2013.01); *A61K 2035/124* (2013.01); *A61K 31/192* (2013.01)

(58) Field of Classification Search
CPC ................................................ A61K 2035/124
USPC ................................ 424/97.3; 514/563, 569
See application file for complete search history.

(56) References Cited

U.S. PATENT DOCUMENTS

| | | | |
|---|---|---|---|
| 4,847,376 A | 7/1989 | Neumann et al. | |
| 5,202,456 A | 4/1993 | Rando | |
| 5,358,972 A | 10/1994 | Buck et al. | |
| 5,475,029 A | 12/1995 | Bradfute et al. | |
| 5,705,528 A | 1/1998 | Kloog | |
| 5,721,103 A | 2/1998 | Boehm et al. | |
| 5,770,378 A | 6/1998 | Hwang et al. | |
| 5,814,612 A | 9/1998 | Buck et al. | |
| 6,207,802 B1 | 3/2001 | Zsebo et al. | |
| 6,239,284 B1 | 5/2001 | Leblond et al. | |
| 6,603,012 B2 | 8/2003 | Belloni et al. | |
| 6,831,082 B2 | 12/2004 | Ingraham et al. | |
| 6,890,925 B2 | 5/2005 | Ingraham et al. | |
| 6,891,062 B2 | 5/2005 | Oida et al. | |
| 7,115,267 B2 | 10/2006 | Wolpe et al. | |
| RE39,682 E | 6/2007 | Kloog | |
| 7,348,359 B2 | 3/2008 | Gardinier et al. | |
| 7,449,495 B2 | 11/2008 | Dallavalle et al. | |
| 7,625,752 B2 | 12/2009 | Casper et al. | |
| 8,168,428 B2 | 5/2012 | Zon et al. | |
| 2002/0077355 A1 | 6/2002 | Liao et al. | |
| 2002/0115586 A1 | 8/2002 | Enikolopov et al. | |
| 2005/0008624 A1* | 1/2005 | Peled et al. ................ | 424/93.21 |
| 2005/0054103 A1 | 3/2005 | Peled et al. | |
| 2005/0074435 A1 | 4/2005 | Casper et al. | |
| 2005/0101599 A1 | 5/2005 | Zeiher et al. | |
| 2005/0238666 A1 | 10/2005 | Williams et al. | |
| 2007/0185070 A1 | 8/2007 | Pershadsingh | |
| 2008/0194534 A1 | 8/2008 | DeLuca et al. | |
| 2009/0111791 A1 | 4/2009 | De Lombaert et al. | |
| 2011/0009370 A1 | 1/2011 | Zon et al. | |
| 2012/0189592 A1 | 7/2012 | Zon et al. | |
| 2012/0189593 A1 | 7/2012 | Zon et al. | |
| 2012/0189594 A1 | 7/2012 | Zon et al. | |

FOREIGN PATENT DOCUMENTS

| | | |
|---|---|---|
| EP | 0356866 A2 | 3/1990 |
| EP | 1563846 B1 | 8/2005 |
| JP | 2009530408 A | 8/2009 |
| RU | 2259830 | 9/2005 |
| WO | 92/18465 A1 | 10/1992 |
| WO | 95/06112 A1 | 3/1995 |
| WO | 95/13059 A1 | 5/1995 |
| WO | 96/40866 A1 | 12/1996 |
| WO | 00/50568 A2 | 8/2000 |
| WO | 2004/032965 A1 | 4/2004 |
| WO | 2004/078169 A1 | 9/2004 |
| WO | 2005/017115 A2 | 2/2005 |

(Continued)

OTHER PUBLICATIONS

Fabian et al. Cancer Research (1986) 46: 2413-2415.*
Attar et al., Leukemia, 18:1760-1768 (2004). "Regulation of hematopoietic stem cell growth."
Barker et al., Nature, 5:997-1014 (2006). "Mining the Wnt pathway for cancer therapeutics."
Bug et al., Cancer Res, 65(7):2537-2541 (2005). "Valproic Acid Stimulates Proliferation and Self-renewal of Hematopoietic Stem Cells."
Cohn et al., J. Clin. Invest., 99(6):1367-1379 (1997). "Crypt Stem Cell Survival in the Mouse Intestinal Epithelium Is Regulated by Prostaglandins Synthesized through Cyclooxygenase-1."

(Continued)

*Primary Examiner* — Susan Hanley
(74) *Attorney, Agent, or Firm* — Nixon Peabody LLP

(57) ABSTRACT

Described herein are methods for enhancing engraftment of hematopoietic stem and progenitor cells using compounds identified using a zebrafish model of hematopoietic cell engraftment. The compounds can be used to treat hematopoietic stem cells ex vivo prior to transplantation of the cells. Alternatively, the compounds can be administered to an individual undergoing cell transplantation.

11 Claims, 7 Drawing Sheets

(56) References Cited

FOREIGN PATENT DOCUMENTS

| | | |
|---|---|---|
| WO | 2005/056024 A1 | 6/2005 |
| WO | 2006/005153 A1 | 1/2006 |
| WO | 2006/078886 A2 | 7/2006 |
| WO | 2006/086639 A1 | 8/2006 |
| WO | 2007/070964 A1 | 6/2007 |
| WO | 2007/112084 A2 | 10/2007 |
| WO | 2008/021475 A2 | 2/2008 |
| WO | 2008/056963 A1 | 5/2008 |

OTHER PUBLICATIONS

Davidson et al., Oncogene, 23:7233-7246 (2004). "The 'definitive' (and 'primitive') guide to zebrafish hematopoiesis."

Desplat et al., Experimental Hematology, 28:741-742 (2000). "Is the COX-2 effect on accelerated hematopoiesis mediated by prostaglandin E2?"

Dupuis et al., Prostaglandins & Other Lipid Mediators, 55:179-186 (1998). "Prostaglandin E2 Stimulates the Growth of Human Blood CD34+ Progenitors."

Feher, Nature, 247:550-551 (1974). "Prostaglandin E2 as stimulator of haemopoietic stem cell proliferation."

Galloway et al., Curr Top Dev Biol, 53:139-158 (2003). "Ontogeny of hematopoiesis: examining the emergence of hematopoietic cells in the vertebrate embryo."

Gentile et al., Blood, 62(5):1100-1107 (1983). "In Vivo Modulation of Murine Myelopoiesis Following Intravenous Administration of Prostaglandin E2."

Gidali et al., Cell Tissue Kinet., 10(4):365-373 (1977). "The effect of E. type prostaglandins on the proliferation of haemopoietic stem cells in vivo."

Goessling et al., Developmental Biology, 320:161-174 (2008). "APC mutant zebrafish uncover a changing temporal requirement for Wnt signaling in liver development."

Goessling et al., Cell, 136:1136-1147 (2009). "Genetic interaction of PGE2 and Wnt signaling regulates developmental specification of stem cells and regeneration."

Guastalla et al., Bull. Cancer, 91:S99-108 Abstract only (2004). "Cyclooxygenase 2 and breast cancer. From biological concepts to therapeutic trials."

Hanson et al., Radiation Research, 103(2):196-203 (1985). "16, 16-dimethyl prostaglandin E-2 induces radioprotection in murine intestinal and hematopoietic stem cells."

Hsia et al., Experimental Hematology, 33:1007-1014 (2005). "Transcriptional regulation of hematopoietic stem cell development in zebrafish."

Huzoor-Akbar et al., Proc. Natl. Acad. Sci., 90:868-872 (1993). "Protein prenylcysteine analog inhibits agonist-receptor-mediated signal transduction in human platelets.".

Janssens et al., Investigational New Drugs, 24:263-280 (2006). "The Wnt-dependent signaling pathways as target in oncology drug discovery."

Kamel et al., "Potential interaction of prostaglandin and Wnt signaling pathways mediating bone cell responses to fluid flow", Journal of Bone and Mineral Research, vol. 21, Nr. Suppl. 1, p. S92, Sep. 15-19, 2006, abstract No. F166.

Kanno et al., PNAS, 101 (33):12277-12281 (2004). "Nitric oxide facilitates cardiomyogenesis in mouse embryonic stem cells."

Kataoka et al., Journal of Gastroenterology, 40(6):610-616 (2005). "Prostaglandin E2 receptor EP4 agonist induces Bcl-xL and independently activates proliferation signals in mouse primary hepatocytes."

Kishi et al., Arch Dis Child, 71(2):153-155 (1994). "Bone marrow suppression induced by high dose valproic acid."

Konturek et al., Journal of Physiology and Pharmacology, 56 (Supp 5):5-31 (2005). "Prostaglandins and ulcer healing."

Krishnan et al., J Clin Invest, 116(5):1202-1209 (2006). "Regulation of bone mass by Wnt signaling."

Lee et al., Journal of Neuroimmunology, 155:21-31 (2004). "Mechanisms involved in prostaglandin E2-mediated neuroprotection against TNF-alpha: possible involvement of multiple signal transduction and beta-catenin/T-Cell factor."

Li et al., American Society of Hematology, 50th ASH annual meeting and exposition, San Francisco, Dec. 6-9, 2008. http://www.ash.confex.com/ash/2008/webprogram/Paper10217.html, accessed Jan. 8, 2009. "Direct Fluorescent Visualization of HSC Competitive Repopulation in Transparent Adult Zebrafish," abstract No. 364.

North and Zon, Developmental Dynamics, 228:568-583 (2003). "Modeling human hematopoietic and cardiovascular diseases in zebrafish."

North et al., Nature, 447:1007-1011 (2007). "Prostaglandin E2 regulates vertebrate haematopoietic stem cell homeostasis."

Okamoto et al., J. Gastroenterol, 39:1-6 (2004). "Molecular and clinical basis for the regeneration of human gastrointestinal epithelia."

Okunieff et al., International Journal of Radiation Oncology, Biology, Physics, 16(5):1145-1148 (1989). "Effects of hydralazine on in vivo tumor energy metabolism, hematopoietic radiation sensitivity, and cardiovascular parameters."

Schmidt et al., Journal of Surgical Research, 41:367-377 (1986). Influence of Prostaglandin on Repair of Rat Stomach Damaged by Absolute Ethanol.

Tan et al., The Journal of Biological Chemistry, 266(17):10719-10722 (1991). "Identifying the Recognition Unit for G Protein Methylation."

Traver et al., Nature, 4(12):1238-1246 (2003). "Transplantation and in vivo imaging of multilineage engraftment in zebrafish bloodless mutants."

Tseng et al., Chemistry & Biology, 13:957-963 (2006). "The GSK-3 inhibitor BIO promotes proliferation in mammalian cardiomyocytes."

Urakawa et al., "Study of 16, 16-dimethyl prostaglandin E2 for prevention of stress ulcer after hepatectomy of experimental cirrhotic liver and its influence on hepatic regeneration", Database EMBASE [online] 1990.

White et al., Cell Stem Cell, 2:183-189 (2008). "Transparent Adult Zebrafish as a Tool for In Vivo Transplantation Analysis."

Zon et al., Nature Reviews, Drug Discovery, 4:35-44 (2005). "In Vivo Drug Discovery in the Zebrafish."

Cancelas et al., Experimental Hematology, 34:976-985 (2006). "The role of chemokine activation of Rac GTPases in hematopoietic stem cell marrow homing, retention, and peripheral mobilization."

De Jong et al., Annu. Rev. Genet., 39:481-501 (2005). "Use of the Zebrafish System to Study Primitive and Definitive Hematopoiesis."

Gur et al., Blood, 99:4174-4181 (2002). "Tolerance induction by megadose hemapoietic progenitor cells: expansion of veto cells by short-term culture of purified human CD34+ cells."

Martelli et al., Seminars in Hematology, 39(1):48-56 (2002). Transplants Across Human Leukocyte Antigen Barriers.

Philips et al., Science, 259:977-980 (1993). "Carboxyl Methylation of Ras-Related Proteins During Signal Transduction in Neutrophils."

Sankaranarayanan et al., Int. J. Radiat. Biol., 67(1):47-55 (1995). "Radioprotective effects of prostaglandins for chromosomal aberrations and cell killing in V79 Chinese hamster cells grown as spheroids in vitro and for mouse spermatogonia) stem cells and bone marrow cells in vivo."

Shao et al., Gastroenterology, 128(4):A146 (2005). "Prostaglandin E2 induces VEGF expression via the Wnt pathway."

Slavin et al., Journal of Clinical Immunology, 22(2):64-69 (2002). "Treatment of Leukemia by Alloreactive Lymphocytes and Nonmyeloablative Stem Cell Transplantation."

Slavin et al., Journal of Hematotherapy & Stem Cell Research, 11:265-276 (2002). "Donor Lymphocyte Infusion: The Use of Alloreactive and Tumor-Reactive Lymphocytes for Immunotherapy of Malignant and Nonmalignant Diseases in Conjunction with Allogeneic Stem Cell Transplantation."

Stier et al., Blood, 99:2369-2378 (2002). "Notch1 activation increases hematopoietic stem cell self-renewal in vivo and favors lymphoid over myeloid lineage outcome."

Traver et al., Blood, 104:1298-1305 (2004). "Effects of lethal irradiation in zebrafish and rescue by hematopoietic cell transplantation."

\* cited by examiner

METHODS FOR ENHANCING HEMATOPOIETIC STEM/PROGENITOR CELL ENGRAFTMENT

CROSS REFERENCE TO RELATED APPLICATIONS

The present application is a 35 U.S.C. 371 National Phase Entry Application of International Application No. PCT/US2010/022992 filed Feb. 3, 2010, which designates the U.S. and which claims the benefit under 35 U.S.C. §119(e) of U.S. Provisional Application No. 61/149,499, filed Feb. 3, 2009, and U.S. Provisional Application No. 61/186,929, filed Jun. 15, 2009, and U.S. Provisional Application No. 61/223,790, filed Jul. 8, 2009, the contents of which are incorporated herein by reference in their entireties.

FIELD OF THE INVENTION

The field of the invention relates to enhancing hematopoietic stem cell and progenitor cell engraftment following transplantation.

BACKGROUND

Hematopoietic stem and progenitor cell transplantation is used for the treatment of a wide variety of hematologic disorders, malignancies, and genetic diseases of the blood. For example, hematopoietic progenitor cell transplantation is currently used to treat bone marrow destruction caused by irradiation and/or alkylating therapy in the treatment of cancer.

Hematopoietic progenitor cells are responsible for hematopoietic recovery during the early post-transplant period. However, in some cases progenitor cell engraftment fails to occur due to e.g., micro-environmental defects as part of the underlying disease (e.g., aplastic anemia), stromal cell damage caused by chemoradiotherapy and development of graft-versus-host disease. In some cases, long-term engraftment and hematopoietic recovery also fails to occur. The failure of long-term engraftment to occur is attributed to the lack of cellular engraftment of hematopoietic stem cells.

Hematopoietic stem cells are capable of self-renewal and as such are responsible for maintaining engraftment over prolonged periods of time (e.g., "long-term engraftment").

Thus, there is a need for the development of methods that improve engraftment of hematopoietic progenitor cells and hematopoietic stem cells.

SUMMARY OF THE INVENTION

Described herein are methods for enhancing engraftment of hematopoietic stem and progenitor cells using compounds of Formula (I) and/or a compound selected from the group consisting of: 1,2-didecanoyl-glycerol (10:0), 11,12 Epoxyeicosatrienoic acid (11,12 EET), 1-hexadecyl-2arachidonoyl glycerol, 6-formylindolo[3,2-B]carbazole, 9-cis-retinoic acid, anandamide, carbacyclin, clofibrate, carbamyl PAF (C-PAF), Prostaglandin B2,5-hydroxydecanoate, and 1,2-dioctanoyl-sn-glycerol (DOG). The compounds can be used to treat hematopoietic stem cells ex vivo prior to transplantation of the cells. Alternatively, the compounds can be administered to an individual undergoing cell transplantation.

In one aspect, the methods described herein relate to enhancing hematopoietic cell engraftment in a subject, the method comprising: (a) contacting a population of hematopoietic cells with a compound of Formula I

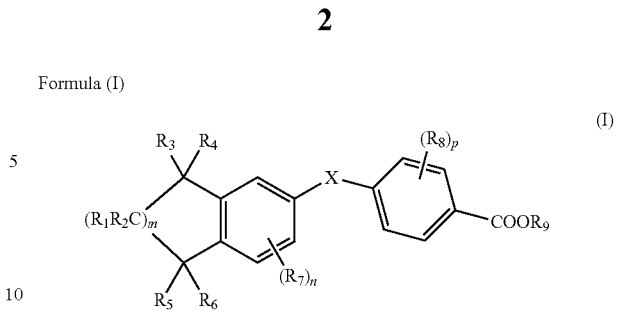

Formula (I)

wherein X is selected from the group consisting of: O, S, SS, $NR_{10}$, C(O), OC(O), C(O)O, $NR_{10}$C(O), C(O)$NR_{10}$, C(S)$NR_{10}$, $NR_{10}$C(S), C(O)S, SC(O), SC($R_{10}$)$_2$, C($R_{10}$)$_2$S, optionally substituted $C_1$-$C_6$ alkyl, optionally substituted $C_2$-$C_6$ alkenyl, optionally substituted $C_2$-$C_6$ alkynyl, C(O)C($R_{10}$)$_2$, C($R_{10}$)$_2$C(O), OC($R_{10}$)$_2$, C($R_{10}$)$_2$O, $NR_{10}$C($R_{10}$)$_2$, C($R_{10}$)$_2$$NR_{10}$, $CR_{10}$=$CR_{10}$, C(O)$CR_{10}$=$CR_{10}$, $CR_{10}$=$CR_{10}$C(O), C($R_{10}$)=N, N=C($R_{10}$), N=N, $N^+(O^-)$=N, N=$N^+(O^-)$ and

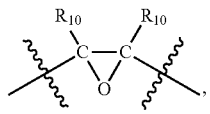

wherein $R_1$, $R_2$, $R_3$, $R_4$, $R_5$ and $R_6$ are independently for each occurrence hydrogen or optionally substituted $C_1$-$C_6$ alkyl, optionally substituted $C_2$-$C_6$ alkenyl, optionally substituted $C_2$-$C_6$ alkynyl, aryl or heteroaryl, wherein $R_7$ and $R_8$ are independently for each occurrence halogen, hydroxyl, SH, optionally substituted $C_1$-$C_6$ alkyl, optionally substituted $C_1$-$C_{10}$ alkoxy, optionally substituted $C_1$-$C_6$ alkylthio, nitro or cyano; and (b) administering treated cells from step (a) to a subject in need thereof, wherein the engraftment of the hematopoietic cells treated with the compound is increased compared to engraftment of a population of untreated hematopoietic cells.

In one embodiment of this aspect and all other aspects described herein, the compound has a structure of

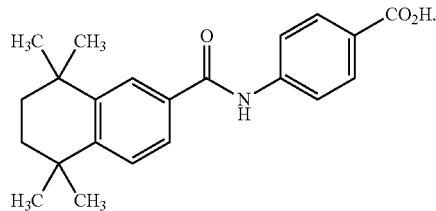 [SMILES: CC1(C)CCC(C)(C)c2cc(C(=O)Nc3ccc(C(=O)O)cc3)ccc21]

In another embodiment of this aspect and all other aspects described herein, the compound has a structure of

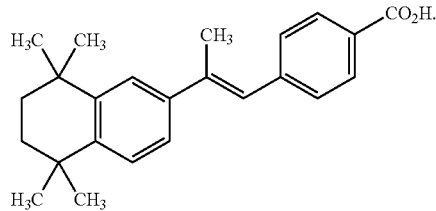 [SMILES: C/C(=C\c1ccc(C(=O)O)cc1)c1ccc2c(c1)C(C)(C)CCC2(C)C]

Also provided are methods for enhancing hematopoietic cell engraftment in a subject, the method comprising: (a) contacting a population of hematopoietic cells with at least one compound selected from the group consisting of: 1,2-didecanoyl-glycerol (10:0), 11,12 Epoxyeicosatrienoic acid (11,12 EET), 1-hexadecyl-2arachidonoyl glycerol, 6-formylindolo[3,2-B]carbazole, 9-cis-retinoic acid, anandamide, carbacyclin, clofibrate, carbamyl PAF (C-PAF), Prostaglandin B2, 5-hydroxydecanoate, and 1,2-dioctanoyl-sn-glycerol (DOG).

In one aspect, the compound is 1,2-didecanoyl-glycerol (10:0).

In one embodiment of this aspect and all other aspects described herein, the compound has a structure of

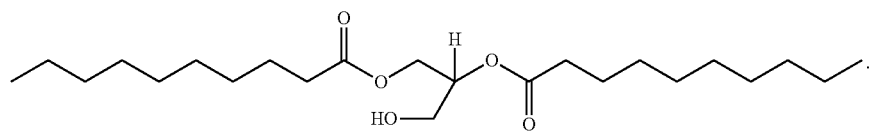 [SMILES: CCCCCCCCCC(=O)OCC(CO)OC(=O)CCCCCCCCC]

In another aspect, the compound is 11,12 Epoxyeicosatrienoic acid (11,12 EET).

In one embodiment of this aspect and all other aspects described herein, the compound has a structure of

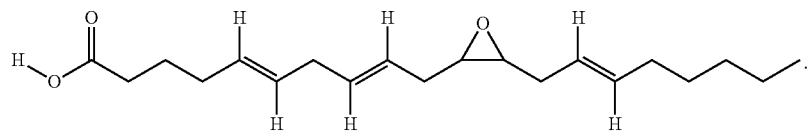 [SMILES: CCCCC/C=C/CC1OC1C/C=C/C/C=C/CCCC(=O)O]

In another aspect, the compound is 1-hexadecyl-2arachidonoyl glycerol.

In another aspect, the compound is 6-formylindolo [31-B] carbazole.

In one embodiment of this aspect and all other aspects described herein, the compound has a structure of

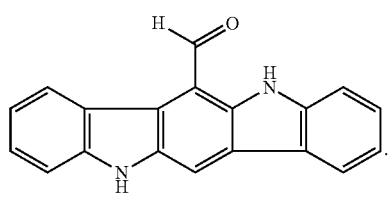 [SMILES: O=Cc1c2[nH]c3ccccc3c2cc2[nH]c3ccccc3c12]

In another aspect, the compound is 9-cis-retinoic acid.

In one embodiment of this aspect and all other aspects described herein, the compound has a structure of

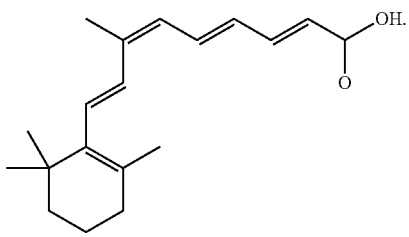 [SMILES: CC1=C(/C=C/C(C)=C\C=C\C=C\C(O)O)C(C)(C)CCC1]

In another aspect, the compound is anandamide.

In one embodiment of this aspect and all other aspects described herein, the compound has a structure of

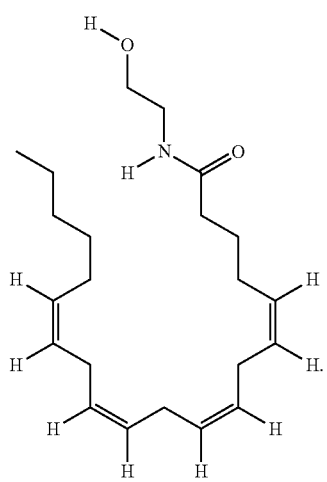

In another aspect, the compound is carbacyclin.

In one embodiment of this aspect and all other aspects described herein, the compound has a structure of

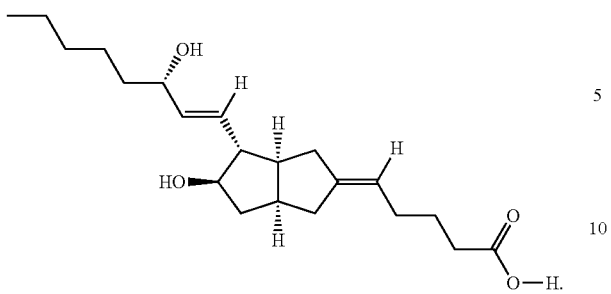

In another aspect, the compound is clofibrate.

In one embodiment of this aspect and all other aspects described herein, the compound has a structure of

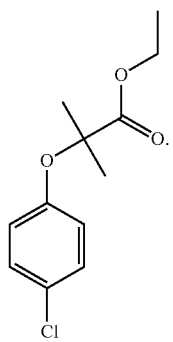 [SMILES: CCOC(=O)C(C)(C)Oc1ccc(Cl)cc1]

In another aspect, the compound is carbamyl-PAF (C-PAF).

In one embodiment of this aspect and all other aspects described herein, the compound has a structure of

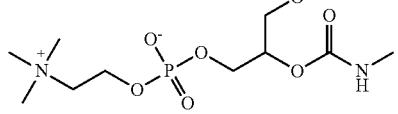

In another aspect, the compound is prostaglandin B2.

In one embodiment of this aspect and all other aspects described herein, the compound has a structure of

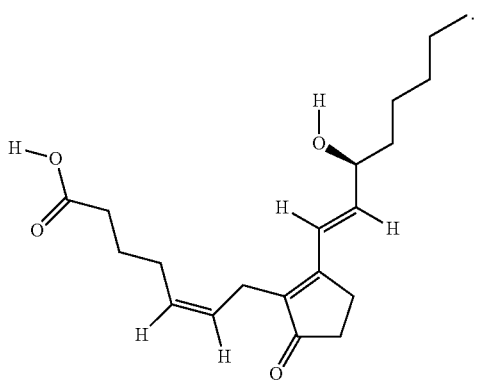 [SMILES: CCCCC[C@H](O)/C=C/C1=C(C/C=C\CCCC(=O)O)C(=O)CC1]

In another aspect, the compound is 5-hydroxydecanoate.

In one embodiment of this aspect and all other aspects described herein, the compound has a structure of

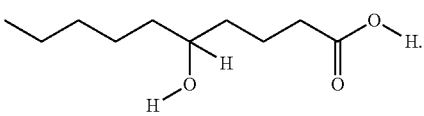

In another aspect, the compound is 14,15-Epoxyeicosa-trienoic acid.

In one embodiment of this aspect and all other aspects described herein, the compound has a structure of

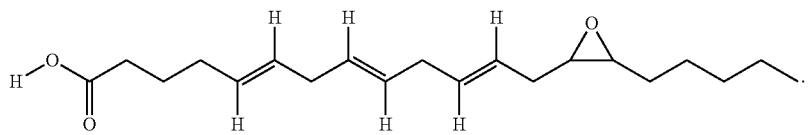 [SMILES: CCCCCC1OC1C/C=C/C/C=C/C/C=C/CCCC(=O)O]

In another aspect, the compound is 1,2-dioctanoyl-sn-glycerol (DOG).

In one embodiment of this aspect and all other aspects described herein, the compound has a structure of

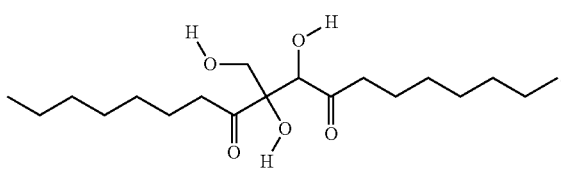 [SMILES: CCCCCCCC(=O)C(O)C(O)(CO)C(=O)CCCCCCC]

In another embodiment of this aspect and all other aspects described herein, the population of hematopoietic cells is derived from cord blood.

In another embodiment of this aspect and all other aspects described herein, the population of hematopoietic cells is derived from bone marrow.

In another embodiment of this aspect and all other aspects described herein, the population of hematopoietic cells is derived from blood.

In another embodiment of this aspect and all other aspects described herein, the population of hematopoietic cells are isolated cells.

In another embodiment of this aspect and all other aspects described herein, the population of hematopoietic cells is a heterogeneous or homogeneous population of cells.

In another embodiment of this aspect and all other aspects described herein, the contacting step is performed on ex vivo cells in culture.

In another embodiment of this aspect and all other aspects described herein, wherein the subject is a human subject.

In another embodiment of this aspect and all other aspects described herein, wherein the hematopoietic cells are hematopoietic stem cells.

In another embodiment of this aspect and all other aspects described herein, the hematopoietic cells are hematopoietic progenitor cells.

Another aspect described herein relates to a method for enhancing hematopoietic cell engraftment in a subject following hematopoietic cell transplantation, the method comprising: administering to a subject following hematopoietic cell transplantation a therapeutically effective amount of a compound of Formula I:

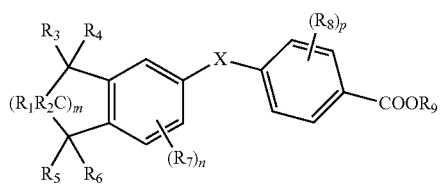

wherein X is selected from the group consisting of: O, S, SS, $NR_{10}$, C(O), OC(O), C(O)O, $NR_{10}C(O)$, $C(O)NR_{10}$, C(S)

$NR_{10}$, $NR_{10}C(S)$, C(O)S, SC(O), $SC(R_{10})_2$, $C(R_{10})_2S$, optionally substituted $C_1$-$C_6$ alkyl, optionally substituted $C_2$-$C_6$ alkenyl, optionally substituted $C_2$-$C_6$ alkynyl, $C(O)C(R_{10})_2$, $C(R_{10})_2C(O)$, $OC(R_{10})_2$, $C(R_{10})_2O$, $NR_{10}C(R_{10})_2$, $C(R_{10})_2NR_{10}$, $CR_{10}=CR_{10}$, $C(O)CR_{10}=CR_{10}$, $CR_{10}=CR_{10}C(O)$, $C(R_{10})=N$, $N=C(R_{10})$, $N=N$, $N^+(O^-)=N$, $N=N^+(O^-)$ and

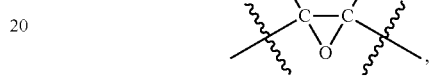

wherein $R_1$, $R_2$, $R_3$, $R_4$, $R_5$ and $R_6$ are independently for each occurrence hydrogen or optionally substituted $C_1$-$C_6$ alkyl, optionally substituted $C_2$-$C_6$ alkenyl, optionally substituted $C_2$-$C_6$ alkynyl, aryl or heteroaryl, wherein $R_7$ and $R_8$ are independently for each occurrence halogen, hydroxyl, SH, optionally substituted $C_1$-$C_6$ alkyl, optionally substituted $C_1$-$C_{10}$ alkoxy, optionally substituted $C_1$-$C_6$ alkylthio, nitro or cyano; and wherein the level of engraftment of the hematopoietic cells in the subject treated with the compound is increased compared to engraftment of a population of hematopoietic cells in an untreated subject.

In one embodiment of this aspect and all other aspects described herein, the compound has a structure of

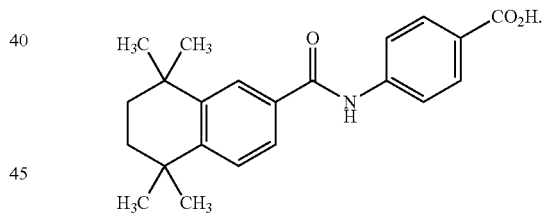

In another embodiment of this aspect and all other aspects described herein, the compound has a structure of

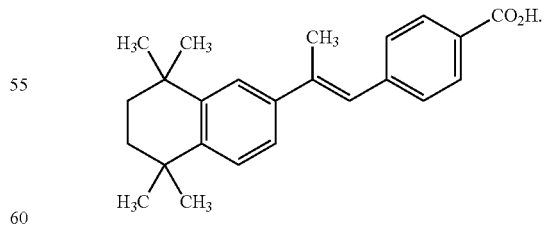

In another embodiment of this aspect and all other aspects described herein, the population of hematopoietic cells is derived from cord blood.

In another embodiment of this aspect and all other aspects described herein, the population of hematopoietic cells is derived from bone marrow.

In another embodiment of this aspect and all other aspects described herein, the population of hematopoietic cells is derived from blood.

In another embodiment of this aspect and all other aspects described herein, the population of hematopoietic cells are isolated cells.

In another embodiment of this aspect and all other aspects described herein, the population of hematopoietic cells is a heterogeneous or homogeneous population of cells.

In another embodiment of this aspect and all other aspects described herein, the subject is a human subject.

In another embodiment of this aspect and all other aspects described herein, the hematopoietic cells are hematopoietic stem cells.

In another embodiment of this aspect and all other aspects described herein, the hematopoietic cells are hematopoietic progenitor cells.

In another aspect, an admixture of hematopoietic stem cells and at least one compound as described herein is administered to a subject.

DEFINITIONS

As used herein, by a "subject" is meant an individual. Thus, subjects include, for example, domesticated animals, such as cats and dogs, livestock (e.g., cattle, horses, pigs, sheep, and goats), laboratory animals (e.g., mice, rabbits, rats, and guinea pigs) mammals, non-human mammals, primates, non-human primates, rodents, birds, reptiles, amphibians, fish, and any other animal. The subject is optionally a mammal such as a primate or a human.

The term "engraftment" is used herein to refer to the ability of hematopoietic stem cells or progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic progenitor cells, or survival of a recipient. In one embodiment, engraftment is determined by measuring white blood cell counts in peripheral blood during a post-transplant period. Alternatively, engraftment can be assessed by measuring recovery of marrow cells in a bone marrow aspirate sample.

As used herein, the term "enhancing hematopoietic cell engraftment" refers to an increase in the efficiency or rate (i.e., amount of engraftment over a period of time) of hematopoietic progenitor cell or stem cell engraftment of at least 10% (e.g., as assessed by measuring white blood cell count) in individuals treated with a compound (or in an individual administered cells treated with an agent) compared to untreated individuals. Preferably the rate of hematopoietic cell engraftment is increased by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 500-fold, at least 1000-fold or higher in individuals being treated with an agent compared to the efficiency/rate of engraftment in an untreated individual. Engraftment can also be assessed using a bone marrow aspirate sample and monitoring colony forming unit cells (CFU-Cs).

As used herein, the term "hematopoietic progenitor cells" encompasses pluripotent cells capable of differentiating into several cell types of the hematopoietic system, including, but not limited to, granulocytes, monocytes, erythrocytes, megakaryocytes, B-cells and T-cells. Hematopoietic progenitor cells are committed to the hematopoietic cell lineage and generally do not self-renew; hematopoietic progenitor cells can be identified, for example by cell surface markers such as Lin−KLS+Flk2−CD34+. The term "hematopoietic progenitor cells" encompasses short term hematopoietic stem cells (ST-HSCs), multi-potent progenitor cells (MPPs), common myeloid progenitor cells (CMPs), granulocyte-monocyte progenitor cells (GMPs), and megakaryocyte-erythrocyte progenitor cells (MEPs). The term "hematopoietic progenitor cells" does not encompass hematopoietic stem cells capable of self-renewal (herein referred to as "hematopoietic stem cells"), which can be identified with the following stem cell marker profile: Lin−KLS+Flk2−CD34−. The presence of hematopoietic progenitor cells can be determined functionally as colony forming unit cells (CFU-Cs) in complete methylcellulose assays, or phenotypically through the detection of cell surface markers using assays known to those of skill in the art.

As used herein, the term "hematopoietic stem cell (HSC)" refers to a cell with multi-lineage hematopoietic differentiation potential and sustained self-renewal activity. "Self renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype. Hematopoietic stem cells have the ability to regenerate long term multi-lineage hematopoiesis (e.g., "long-term engraftment") in individuals receiving a bone marrow or cord blood transplant. The hematopoietic stem cells used may be derived from any one or more of the following sources: fetal tissues, cord blood, bone marrow, peripheral blood, mobilized peripheral blood, a stem cell line, or may be derived ex vivo from other cells, such as embryonic stem cells, induced pluripotent stem cells (iPS cells) or adult pluripotent cells. The cells from the above listed sources may be expanded ex vivo using any method acceptable to those skilled in the art prior to use in the transplantation procedure. For example, cells may be sorted, fractionated, treated to remove malignant cells, or otherwise manipulated to treat the patient using any procedure acceptable to those skilled in the art of preparing cells for transplantation. If the cells used are derived from an immortalized stem cell line, further advantages would be realized in the ease of obtaining and preparation of cells in adequate quantities.

As used herein, the term "population of hematopoietic cells" encompasses a heterogeneous or homogeneous population of hematopoietic stem cells and/or hematopoietic progenitor cells. In addition, differentiated hematopoietic cells, such as white blood cells, can be present in a population of hematopoietic cells; that is, in one embodiment hematopoietic stem and/or progenitor cells are not isolated from e.g., cord blood, bone marrow. A population of hematopoietic cells comprising at least two different cell types is referred to herein as a "heterogeneous population". It is also contemplated herein that hematopoietic stem cells or hematopoietic progenitor cells are isolated and expanded ex vivo prior to transplantation. A population of hematopoietic cells comprising only one cell type (e.g., hematopoietic stem cells) is referred to herein as a "homogeneous population of cells".

"Expansion" or "expanded" in the context of cells refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells. It is contemplated herein that a hematopoietic stem cell or progenitor cell is expanded in culture prior to transplantation into an individual in need thereof.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

DETAILED DESCRIPTION

Figure 1:
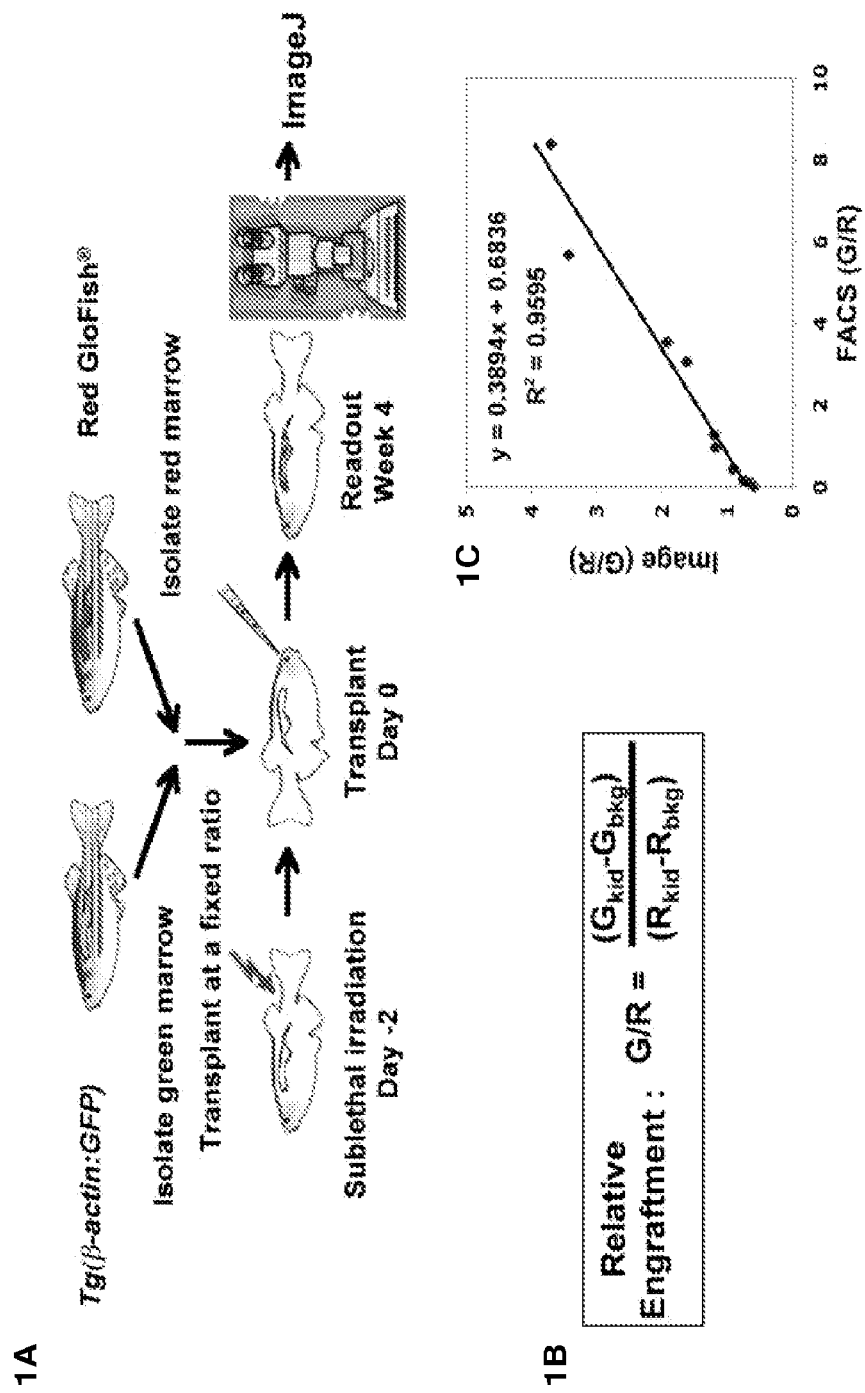
FIGS. 1A-1C show a schematic representation of the design of an exemplary adult zebrafish competitive transplantation assay. 1A) Flow chart of a competitive transplantation in adult zebrafish (casper fish as recipients); 1B) quantification of relative engraftment by image fluorescence analysis. G/R, GFP intensity/DsRed2 intensity; Gkid, kidney GFP intensity; Gbkg, background GFP intensity; Rkid, kidney DsRed2 intensity; Rbkg, background DsRed2 intensity. 1C) positive correlation of FACS analysis results and image fluorescence analysis results. The G/R of FACS analysis is defined by the ratio of the percentage of GFP+ cells over the percentage of DsRed2+ cells.

The methods described herein are based, in part, on the discovery of a class of compounds that enhance engraftment of hematopoietic stem and/or progenitor cells following transplantation, such as a bone marrow or cord blood transplant. Accordingly, provided herein are methods for enhancing engraftment of hematopoietic stem and/or progenitor cells by treating cells ex vivo prior to transplantation to an individual in need thereof. Also provided herein are methods for enhancing engraftment comprising administering a compound as described herein to an individual undergoing a hematopoietic stem and/or progenitor cell transplant.

Hematopoietic Stem/Progenitor Cells

Hematopoietic Stem Cells

Hematopoietic stem cells (HSC) are primitive cells capable of regenerating all blood cells. During development, the site of hematopoiesis translocates from the fetal liver to the bone marrow, which then remains the site of hematopoiesis throughout adulthood.

HSC as used herein refer to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). Hematopoietic stem cells are interchangeably described as stem cells throughout the specification. It is known in the art that such cells may or may not include CD34+ cells. CD34+ cells are immature cells that express the CD34 cell surface marker. CD34+ cells are believed to include a subpopulation of cells with the stem cell properties defined above. It is well known in the art that hematopoietic stem cells include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage and/or lymphoid tissue-specific macrophage cell lineage. In addition, HSCs also refer to long term HSC (LT-HSC) and short term HSC(ST-HSC). A long term stem cell typically includes the long term (more than three months) contribution to multilineage engraftment after transplantation. A short term stem cell is typically anything that lasts shorter than three months, and/or that is not multilineage. LT-HSC and ST-HSC are differentiated, for example, based on their cell surface marker expression. LT-HSC are CD34−, SCA-1+, Thy1.1+/lo, C-kit+, Un−, CD135−, Slamfl/CD150+, whereas ST-HSC are CD34+, SCA-1+, Thy1.1+/lo, C-kit+, lin−, CD135−, Slamfl/CD150+, Mac-1 (CDlIb)lo ("lo" refers to low expression). In addition, ST-HSC are less quiescent (i.e., more active) and more proliferative than LT-HSC. LT-HSC have unlimited self renewal (i.e., they survive throughout adulthood), whereas ST-HSC have limited self renewal (i.e., they survive for only a limited period of time). Any of these HSCs can be used in any of the methods described herein.

HSC are optionally obtained from blood products. A blood product includes a product obtained from the body or an organ of the body containing cells of hematopoietic origin. Such sources include unfractionated bone marrow, umbilical cord, peripheral blood, liver, thymus, lymph and spleen. All of the aforementioned crude or unfractionated blood products can be enriched for cells having hematopoietic stem cell characteristics in a number of ways. For example, the more mature, differentiated cells are selected against, via cell surface molecules they express. Optionally, the blood product is fractionated by selecting for CD34+ cells. CD34+ cells include a subpopulation of cells capable of self-renewal and pluripotentiality. Such selection is accomplished using, for example, commercially available magnetic anti-CD34 beads (Dynal, Lake Success, N.Y.). Unfractionated blood products are optionally obtained directly from a donor or retrieved from cryopreservative storage.

Sources for HSC expansion also include aorta-gonad-mesonephros (AGM) derived cells, embryonic stem cell (ESC) and induced pluripotent stem cells (iPSC). ESC are well-known in the art, and may be obtained from commercial or academic sources (Thomson et al., 282 Sci. 1145-47 (1998)). iPSC are a type of pluripotent stem cell artificially derived from a non-pluripotent cell, typically an adult somatic cell, by inducing a "forced" expression of certain genes (Baker, Nature Rep. Stem Cells (Dec. 6, 2007); Vogel & Holden, 23 Sci. 1224-25 (2007)). ESC, AGM, and iPSC may be derived from animal or human sources. The AGM stem cell is a cell that is born inside the aorta, and colonizes the fetal liver. Signaling pathways can increase AGM stem cells make it likely that these pathways will increase HSC in ESC.

Hematopoietic Progenitor Cells

Hematopoietic progenitor cells, as the term is used herein, are capable of producing all cells types in the hematopoietic lineage, but are not capable of long-term self-renewal. Thus, hematopoietic progenitor cells can restore and sustain hematopoiesis for three to four months (Marshak, D. R., et al. (2001). Stem cell biology, Cold Spring Harbor, N.Y.: Cold Spring Harbor Laboratory Press) and are important for recovery in the period immediately following a hematopoietic progenitor cell transplant in an individual. Hematopoietic progenitor cells useful for transplantation can be obtained from a variety of sources including, for example, bone marrow, peripheral blood, and umbilical cord blood.

Bone marrow can be obtained by puncturing bone with a needle and removing bone marrow cells with a syringe (herein called "bone marrow aspirate"). Hematopoietic progenitor cells can be isolated from the bone marrow aspirate prior to transplantation by using surface markers specific for hematopoietic progenitor cells, or alternatively whole bone marrow can be transplanted into an individual to be treated with the methods described herein.

Hematopoietic progenitor cells can also be obtained from peripheral blood of a progenitor cell donor. Prior to harvest of the cells from peripheral blood, the donor can be treated with a cytokine, such as e.g., granulocyte-colony stimulating factor, to promote cell migration from the bone marrow to the blood compartment. Cells can be collected via an intravenous tube and filtered to isolate white blood cells for transplantation. The white blood cell population obtained (i.e., a mixture of stem cells, progenitors and white blood cells of various degrees of maturity) can be transplanted as a heterogeneous mixture or hematopoietic progenitor cells can further be isolated using cell surface markers known to those of skill in the art.

Hematopoietic progenitor cells and/or a heterogeneous hematopoietic progenitor cell population can also be isolated from human umbilical cord and/or placental blood.

Isolation of Hematopoietic Stem Cells

A hematopoietic stem cell (HSC) population can be obtained from a biopsy removed from a donor employing techniques known by persons skilled in the art, including the removal of stem cells from the bone marrow of a donor from large bone masses utilizing a large needle intended for bone marrow harvesting. Alternatively, HSCs may be collected by apheresis, a process in which a donor's peripheral blood is withdrawn through a sterile needle and passed through a device that removes white blood cells, and that returns the red blood cells to the donor. The peripheral stem cell yield can be increased with daily subcutaneous injections of granulocyte-colony stimulating factor. The HSCs are preferably obtained from human donors, however, non-human donors are also contemplated, including non-human primates, pigs, cows, horses, cats, and dogs. A purified population of HSCs may be obtained by utilizing various methods known by persons skilled in the art and described in U.S. Pat. No. 5,677,136; and U.S. Patent Publication No. 2006/0040389, which are incorporated by reference in their entirety.

In one embodiment described herein, hematopoietic stem cells or progenitor cells are isolated prior to transplantation. Hematopoietic cell samples (e.g., cord blood, peripheral blood, bone marrow) can first be purified to isolate and obtain artificially high concentrations of e.g., HSCs by detecting expression of specific cell surface proteins or receptors, cell surface protein markers, or other markers. Highly purified HSCs are increasingly being used clinically, in a variety of applications, such as for autologous transplants into patients after high-dose chemotherapy. In this setting it is advantageous to isolate HSCs with the maximum degree of purity so as to minimize contamination by immune effector cells (such as lymphocytes) or cancer cells. In murine studies, the highest enrichment of HSC activity yet reported describes combinations of markers, such as those used to isolate Thy-1.1$^{lo}$Sca-1$^+$lineage-Mac-1-CD4$^-$c-kit$^+$ cells, from which about one out of every five intravenously injected cells are able to home to bone marrow and engraft. Such results are described in, for example, Uchida et al.; Morrison et al., 1994 and Morrison et al. 1997 supra).

Stem cells as well as committed progenitor cells destined to become neutrophils, erythrocytes, platelets, etc., may be distinguished from most other cells by the presence or absence of particular progenitor marker antigens, such as CD34, that are present on the surface of these cells and/or by morphological characteristics. The phenotype for a highly enriched human stem cell fraction is reported as CD34$^+$,Thy-1$^+$ and lin$^-$, but it is to be understood that the present invention is not limited to the expansion of this stem cell population.

The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several subpopulations characterized by the presence or absence of coexpression of different lineage associated cell surface associated molecules. The most immature progenitor cells do not express any known lineage-associated markers, such as HLA-DR or CD38, but they may express CD90 (thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various hematopoietic growth factors may be utilized in order to selectively expand cells. Representative factors that have been utilized for ex vivo expansion of bone marrow include, c-kit ligand, IL-3, G-CSF, GM-CSF, IL-1, IL-6, IL-11, flt-3 ligand or combinations thereof. The proliferation of stem cells can be monitored by enumerating the number of stem cells and other cells, by standard techniques (e.g., hemacytometer, CFU, LTCIC) or by flow cytometry prior and subsequent to incubation.

Any method suitable for identifying surface proteins, whether known or to be discovered, could be employed to isolate hematopoietic stem cells from a homogeneous population such as e.g., cord blood. For example, HSCs for use with the methods described herein may be identified using fluorescence activated cell sorting analysis (FACS) which typically uses antibodies conjugated to fluorochromes to directly or indirectly assess the level of expression of a given surface protein on individual cells within a heterogenous (or homogenous) cell preparation of hematopoietic tissue.

HSCs may be physically separated from other cells within a cellular preparation of hematopoietic tissue using any previously developed or as yet undeveloped technique whereby cells are directly or indirectly differentiated according to their expression or lack of expression of particular surface proteins. Common methods used to physically separate specific cells from within a heterogenous population of cells within a hematopoietic cell preparation include but are not limited to flow-cytometry using a cytometer which may have varying degrees of complexity and or detection specifications, magnetic separation, using antibody or protein coated beads, affinity chromatography, or solid-support affinity separation where cells are retained on a substrate according to their expression or lack of expression of a specific protein or type of protein. Such separation techniques need not, but may, completely purify or nearly completely purify (e.g. 99.9% are perfectly separated) HSCs or populations enriched in HSCs.

Cell Culture and Expansion of Isolated Hematopoietic Stem/Progenitor Cells

The expanded population of stem cells are harvested, for example, from a bone marrow sample of a subject or from a culture. Harvesting hematopoietic stem cells is defined as the dislodging or separation of cells. This is accomplished using a number of methods, such as enzymatic, non-enzymatic, centrifugal, electrical, or size-based methods, or preferably, by flushing the cells using culture media (e.g., media in which cells are incubated) or buffered solution. The cells are optionally collected, separated, and further expanded generating even larger populations of HSC and differentiated progeny.

In general, cells useful for the invention can be maintained and expanded in culture medium that is available to and well-known in the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®, and serum-free medium for culture and expansion of hematopoietic cells SFEM®. Many media are also available as low-glucose formulations, with or without sodium pyruvate.

Also contemplated herein is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements and bovine embryonic fluid. It is understood that sera can be heat-inactivated at 55-65° C. if deemed necessary to inactivate components of the complement cascade.

Additional supplements also can be used advantageously to supply the cells with the necessary trace elements for optimal growth and expansion. Such supplements include insulin, transferrin, sodium selenium and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Hormones also can be advantageously used in the cell cultures of the present invention and include, but are not limited to, D-aldosterone, diethylstilbestrol (DES), dexamethasone, .beta.-estradiol, hydrocortisone, insulin, prolactin, progesterone, somatostatin/human growth hormone (HGH), thyrotropin, thyroxine and L-thyronine.

Lipids and lipid carriers also can be used to supplement cell culture media, depending on the type of cell and the fate of the differentiated cell. Such lipids and carriers can include, but are not limited to, cyclodextrin ($\alpha,\beta,\gamma$), cholesterol, linoleic acid conjugated to albumin, linoleic acid and oleic acid conjugated to albumin, unconjugated linoleic acid, linoleic-oleic-arachidonic acid conjugated to albumin and oleic acid unconjugated and conjugated to albumin, among others.

Also contemplated in the present invention is the use of feeder cell layers. Feeder cells are used to support the growth of fastidious cultured cells, such as stem cells. Feeder cells are normal cells that have been inactivated by $\gamma$-irradiation. In culture, the feeder layer serves as a basal layer for other cells and supplies cellular factors without further growth or division of their own (Lim, J. W. and Bodnar, A., 2002). Examples of feeder layer cells are typically human diploid lung cells, mouse embryonic fibroblasts and Swiss mouse embryonic fibroblasts, but can be any post-mitotic cell that is capable of supplying cellular components and factors that are advantageous in allowing optimal growth, viability and expansion of stem cells. In many cases, feeder cell layers are not necessary to keep stem cells in an undifferentiated, proliferative state, as leukemia inhibitory factor (LIF) has anti-differentiation properties. Therefore, supplementation with LIF can be used to maintain cells in an undifferentiated state.

Cells may be cultured in low-serum or serum-free culture medium. Serum-free medium used to culture cells is described in, for example, U.S. Pat. No. 7,015,037. Many cells have been grown in serum-free or low-serum medium. For example, the medium can be supplemented with one or more growth factors. Commonly used growth factors include, but are not limited to, bone morphogenic protein, basic fibroblast growth factor, platelet-derived growth factor and epidermal growth factor, Stem cell factor, thrombopoietin, Flt3Ligand and 1'-3. See, for example, U.S. Pat. Nos. 7,169,610; 7,109,032; 7,037,721; 6,617,161; 6,617,159; 6,372,210;

6,224,860; 6,037,174; 5,908,782; 5,766,951; 5,397,706; and 4,657,866; all incorporated by reference herein for teaching growing cells in serum-free medium.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "superfibronectin" and fibronectin-like polymers, gelatin, poly-D and poly-L-lysine, thrombospondin and vitronectin. Hematopoietic stem cells can also be cultured in low attachment flasks such as but not limited to Corning Low attachment plates.

In one embodiment, hematopoietic stem and/or progenitor cells are treated ex vivo prior to transplantation to an individual in need thereof by contacting a population of hematopoetic cells with the compound of Formula I. Contacting can be performed in vitro by adding the compound of Formula I directly to suitable cell culture medium for hematopoietic cells. The concentration of compound can be determined by those of skill in the art, for example by performing serial dilutions and testing efficacy in the Zebrafish competitive transplant model, or other suitable system. Example concentration ranges for the treatment of the hematopoietic stem and/or progenitor cells include, but are not limited to, about 1 nanomolar to about 10 millimolar; about 1 mM to about 5 mM; about 1 nM to about 500 nM; about 500 nM to about 1,000 nM; about 1 nM to about 1,000 nM; about 1 uM to about 1,000 uM; 1 uM to about 500 uM; about 1 uM to about 100 uM; about 1 uM to about 10 uM. In one embodiment, the range is about 5 uM to about 500 uM.

Cells can be treated for various times. Suitable times can be determined by those of skill in the art. For example, cells can be treated for minutes, 15 minutes, 30 minutes etc, or treated for hours e.g., 1 hour, 2 hours, 3 hours, 4 hours, up to 24 hours or even days. In one embodiment the cells are treated for 2 hours prior to changing to medium without drug.

Cryopreservation of Cells and Blood

Once established in culture, cells treated with the compounds of Formula I (e.g. TTNPB or AM-580), and/or untreated cells can be used fresh or frozen and stored as frozen stocks, using, for example, DMEM with 40% FCS and 10% DMSO. Other methods for preparing frozen stocks for cultured cells also are available to those skilled in the art.

In addition, the stem cells obtained from harvesting according to method of the present invention described above can be cryopreserved using techniques known in the art for stem cell cryopreservation. Accordingly, using cryopreservation, the stem cells can be maintained such that once it is determined that a subject is in need of stem cell transplantation, the stem cells can be thawed and transplanted back into the subject.

More specifically, an embodiment of the present invention provides for the enhancement of HSCs collected from cord blood or an equivalent neonatal or fetal stem cell source, which may be cryopreserved, for the therapeutic uses of such stem cells upon thawing. Such blood may be collected by several methods known in the art. For example, because umbilical cord blood is a rich source of HSCs (see Nakahata & Ogawa, 70 J. Clin. Invest. 1324-28 (1982); Prindull et al., 67 Acta. Paediatr. Scand. 413-16 (1978); Tchernia et al., 97(3) J. Lab. Clin. Med. 322-31 (1981)), an excellent source for neonatal blood is the umbilical cord and placenta. Prior to cryopreservation, the neonatal blood may be obtained by direct drainage from the cord and/or by needle aspiration from the delivered placenta at the root and at distended veins. See, e.g., U.S. Pat. No. 7,160,714; No. 5,114,672; No. 5,004, 681; U.S. patent application Ser. No. 10/076,180, Pub. No. 20030032179. Indeed, umbilical cord blood stem cells have been used to reconstitute hematopoiesis in children with malignant and nonmalignant diseases after treatment with myeloablative doses of chemo-radiotherapy. Sirchia & Rebulla, 84 Haematologica 738-47 (1999). See also Laughlin 27 Bone Marrow Transplant. 1-6 (2001); U.S. Pat. No. 6,852, 534. Additionally, it has been reported that stem and progenitor cells in cord blood appear to have a greater proliferative capacity in culture than those in adult bone marrow. Salahuddin et al., 58 Blood 931-38 (1981); Cappellini et al., 57 Brit. J. Haematol. 61-70 (1984).

Alternatively, fetal blood can be taken from the fetal circulation at the placental root with the use of a needle guided by ultrasound (Daffos et al., 153 Am. J. Obstet. Gynecol. 655-60 (1985); Daffos et al., 146 Am. J. Obstet. Gynecol. 985-87 (1983), by placentocentesis (Valenti, 115 Am. J. Obstet. Gynecol. 851-53 (1973); Cao et al., 19 J. Med. Genet. 81-87 (1982)), by fetoscopy (Rodeck, in PRENATAL DIAGNOSIS, (Rodeck & Nicolaides, eds., Royal College of Obstetricians & Gynaecologists, London, 1984)) and cryopreserved. Indeed, the chorionic villus and amniotic fluid, in addition to cord blood and placenta, are sources of pluripotent fetal stem cells (see WO 2003 042405).

Various kits and collection devices are known for the collection, processing, and storage of cord blood. See, e.g., U.S. Pat. No. 7,147,626; U.S. Pat. No. 7,131,958. Collections should be made under sterile conditions, and the blood may be treated with an anticoagulant. Such anticoagulants include citrate-phosphate-dextrose, acid citrate-dextrose, Alsever's solution (Alsever & Ainslie, 41N.Y. St. J. Med. 126-35 (1941), DeGowin's Solution (DeGowin et al., 114 JAMA 850-55 (1940)), Edglugate-Mg (Smith et al., 38 J. Thorac. Cardiovasc. Surg. 573-85 (1959)), Rous-Turner Solution (Rous & Turner, 23 J. Exp. Med. 219-37 (1916)), other glucose mixtures, heparin, or ethyl biscoumacetate. See Hurn, STORAGE OF BLOOD 26-160 (Acad. Press, NY, 1968).

Various procedures are known in the art or described herein and can be used to enrich collected cord blood for HSCs. These include but are not limited to equilibrium density centrifugation, velocity sedimentation at unit gravity, immune rosetting and immune adherence, counterflow centrifugal elutriation, T-lymphocyte depletion, and fluorescence-activated cell sorting, alone or in combination. See, e.g., U.S. Pat. No. 5,004,681.

Typically, collected blood is prepared for cryogenic storage by addition of cryoprotective agents such as DMSO (Lovelock & Bishop, 183 Nature 1394-95 (1959); Ashwood-Smith 190 Nature 1204-05 (1961)), glycerol, polyvinylpyrrolidine (Rinfret, 85 Ann. N.Y. Acad. Sci. 576-94 (1960)), polyethylene glycol (Sloviter & Ravdin, 196 Nature 899-900 (1962)), albumin, dextran, sucrose, ethylene glycol, i-erythritol, D-ribitol, D-mannitol (Rowe, 3(1) Cryobiology 12-18 (1966)), D-sorbitol, i-inositol, D-lactose, choline chloride (Bender et al., 15 J. Appl. Physiol. 520-24 (1960)), amino acids (Phan & Bender, 20 Exp. Cell Res. 651-54 (1960)), methanol, acetamide, glycerol monoacetate (Lovelock, 56 Biochem. J. 265-70 (1954)), and inorganic salts (Phan & Bender, 104 Proc. Soc. Exp. Biol. Med. (1960)). Addition of plasma (e.g., to a concentration of 20%-25%) may augment the protective effect of DMSO.

Collected blood should be cooled at a controlled rate for cryogenic storage. Different cryoprotective agents and different cell types have different optimal cooling rates. See e.g., Rapatz, 5 Cryobiology 18-25 (1968), Rowe & Rinfret, 20 Blood 636-37 (1962); Rowe, 3 Cryobiology 12-18 (1966); Lewis et al., 7 Transfusion 17-32 (1967); Mazur, 168 Science 939-49 (1970). Considerations and procedures for the manipulation, cryopreservation, and long-term storage of HSC sources are known in the art. See e.g., U.S. Pat. No. 4,199,022; No. 3,753,357; No. 4,559,298; No. 5,004,681. There are also various devices with associated protocols for the storage of blood. U.S. Pat. No. 6,226,997; No. 7,179,643

Considerations in the thawing and reconstitution of HSC sources are also known in the art. U.S. Pat. No. 7,179,643; No. 5,004,681. The HSC source blood may also be treated to prevent clumping (see Spitzer, 45 Cancer 3075-85 (1980); Stiff et al., 20 Cryobiology 17-24 (1983), and to remove toxic cryoprotective agents (U.S. Pat. No. 5,004,681). Further, there are various approaches to determining an engrafting cell dose of HSC transplant units. See U.S. Pat. No. 6,852,534; Kuchler, in BIOCHEM. METHS. CELL CULTURE & VIROLOGY 18-19 (Dowden, Hutchinson & Ross, Strodsburg, Pa., 1964); 10 METHS. MED. RES. 39-47 (Eisen, et al., eds., Year Book Med. Pub., Inc., Chicago, Ill., 1964).

Diseases of the Hematopoietic System

Hematopoietic progenitor cells or stem cells can be transplanted to regenerate hematopoietic cells in an individual having a disease of the hematopoietic system. Such diseases can include, but are not limited to, cancers (e.g., leukemia, lymphoma), blood disorders (e.g., inherited anemia, inborn errors of metabolism, aplastic anemia, beta-thalassemia, Blackfan-Diamond syndrome, globoid cell leukodystrophy, sickle cell anemia, severe combined immunodeficiency, X-linked lymphoproliferative syndrome, Wiskott-Aldrich syndrome, Hunter's syndrome, Hurler's syndrome Lesch Nyhan syndrome, osteopetrosis), chemotherapy rescue of the immune system, and other diseases (e.g., autoimmune diseases, diabetes, rheumatoid arthritis, system lupus erythromatosis).

Compounds

In one aspect, compounds useful with the methods described herein relate to a compound of formula (I):

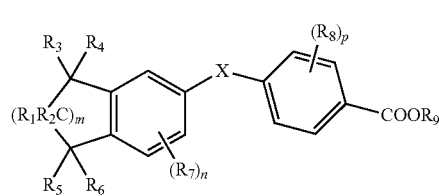

(I)

wherein X is O, S, SS, $NR_{10}$, C(O), OC(O), C(O)O, $NR_{10}C(O)$, $C(O)NR_{10}$, $C(S)NR_{10}$, $NR_{10}C(S)$, C(O)S, SC(O), $SC(R_{10})_2$, $C(R_{10})_2S$, optionally substituted $C_1$-$C_6$ alkyl, optionally substituted $C_2$-$C_6$ alkenyl, optionally substituted $C_2$-$C_6$ alkynyl, $C(O)C(R_{10})_2$, $C(R_{10})_2C(O)$, $OC(R_{10})_2$, $C(R_{10})_2O$, $NR_{10}C(R_{10})_2$, $C(R_{10})_2NR_{10}$, $CR_{10}$=$CR_{10}$, C(O) $CR_{10}$=$CR_{10}$, $CR_{10}$=$CR_{10}C(O)$, $C(R_{10})$=N, N=$C(R_{10})$, N=N, $N^+(O^-)$=N, N=$N^+(O^-)$ or

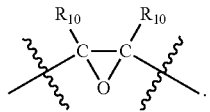

Preferably X is OC(O), C(O)O, $NR_{10}C(O)$, $C(O)NR_{10}$, $CR_{10}$=$CR_{10}$, $CH_2CH_2$, $C(O)C(R_{10})_2$, $C(R_{10})_2C(O)$, $OC(R_{10})_2$, $C(R_{10})_2O$, $C(R_{10})$=N, N=$C(R_{10})$, or N=N. In a preferred embodiment, X is $NR_{10}C(O)$, $C(O)NR_{10}$ or $CR_{10}$=$CR_{10}$. In a most preferred embodiment, X is C(O)NH or $C(CH_3)$=CH. When X is capable of cis-trans conformation isomers, isomers with the two aromatic rings of formula (I) being trans to each other are preferred. Thus in a preferred embodiment, $C(CH_3)$=CH, has the trans conformation at the double bond.

$R_1$, $R_2$, $R_3$, $R_4$, $R_5$ and $R_6$ are independently for each occurrence hydrogen or optionally substituted $C_1$-$C_6$ alkyl, optionally substituted $C_2$-$C_6$ alkenyl, optionally substituted $C_2$-$C_6$ alkynyl, aryl or heteroaryl. Preferably $R_1$, $R_2$, $R_3$, $R_4$, $R_5$ and $R_6$ are independently for each occurrence hydrogen or optionally substituted $C_1$-$C_6$ alkyl. In one embodiment, $R_3$, $R_4$, $R_5$ and $R_6$ are $CH_3$. Preferably $R_1$ and $R_2$ are hydrogen or optionally substituted $C_1$-$C_6$ alkyl. Most preferably $R_1$ and $R_2$ are hydrogen.

$R_7$ and $R_8$ are independently for each occurrence halogen, hydroxyl, SH, optionally substituted $C_1$-$C_6$ alkyl, optionally substituted $C_1$-$C_{10}$ alkoxy, optionally substituted $C_1$-$C_6$ alkylthio, nitro or cyano. In one embodiment $R_7$ and $R_8$ are independently halogen, hydroxyl or optionally substituted $C_1$-$C_6$ alkyl. Preferred halogens include fluorine and bromine.

$R_9$ is hydrogen or optionally substituted $C_1$-$C_6$ alkyl. In one embodiment $R_9$ is hydrogen, $CH_3$, $CH_2CH_3$, $CH_2CH_2CH_3$ or $CH_2CH_2CH_2CH_3$. In one embodiment, $R_9$ is hydrogen. In one embodiment, $R_3$ is $CH_3$.

$R_{10}$ is independently for each occurrence hydrogen, hydroxyl or optionally substituted $C_1$-$C_6$ alkyl. In one embodiment $R_{10}$ is independently for each occurrence hydrogen or $C_1$-$C_4$ alkyl. In one embodiment, $R_{10}$ is hydrogen.

The variable m is an integer from 1-4. In one embodiment, n ranges from 1-3, and is most preferably 2. The variable n is an integer from 0 to 3. In one embodiment, n ranges from 0-1, and is most preferably 0. The variable p is an integer from 0 to 4. In one embodiment, n ranges from 0-4, and is most preferably 0.

The compounds of formula (I) include salts, e.g., pharmaceutically acceptable salts, stereoisomer mixtures, and enantiomers thereof. The optionally substituted $C_1$-$C_6$ alkyl may contain one or more heteroatoms such as O, N, or S.

In certain embodiments, m is 1, 2 or 3.

In one embodiment, m is 1 or 2, n is 1-3 and p is 0. In another embodiment, m is 1 or 2, n is 0 and p is 1-4. In yet another embodiment, m is 1 or 2, n is 1-3 and p is 1-4. In still yet another embodiment, m is 1 or 2, n is 0 and p is 0.

In one embodiment, at least one of $R_3$, $R_4$, $R_5$ and $R_6$ is aryl or heteroaryl.

In one embodiment, $R_2$ and $R_3$ together form a bond between the carbons to which $R_2$ and $R_3$ are attached. In another embodiment, $R_2$ and $R_3$ from a 5-8 membered ring. In yet another embodiment, $R_2$ and $R_5$ from a 5-8 membered ring.

In another embodiment, m is 2 and $R_2$ and $R_3$ together form a bond between the carbons to which $R_2$ and $R_3$ are attached.

In yet another embodiment, m is 2, $R_2$ and $R_3$ together form a bond between the carbons to which $R_2$ and $R_3$ are attached and $R_4$ is a heteroaryl.

In a preferred embodiment of the compound, m is 2, $R_1$ and $R_2$ are hydrogen, $R_3$, $R_4$, $R_5$ and $R_6$ are $CH_3$, X is C(O)NH or NH(CO) and $R_9$ is hydrogen or $CH_3$.

In a more preferred embodiment of the compound m is 2, n is 0, p is 0, $R_1$ and $R_2$ are hydrogen, $R_3$, $R_4$, $R_5$ and $R_6$ are $CH_3$, X is C(O)NH or NH(CO) and $R_9$ is hydrogen or $CH_3$.

In yet another preferred embodiment of the compound, m is 2, $R_1$ and $R_2$ are hydrogen, $R_3$, $R_4$, $R_5$ and $R_6$ are $CH_3$, X is $C(CH_3)=CH$ and $R_9$ is hydrogen or $CH_3$.

In a still more preferred embodiment of the compound, m is 2, n is 0, p is 0, $R_1$ and $R_2$ are hydrogen, $R_3$, $R_4$, $R_5$ and $R_6$ are $CH_3$, X is $C(CH_3)=CH$ and $R_9$ is hydrogen or $CH_3$.

In a most preferred embodiment, the compound has the structure:

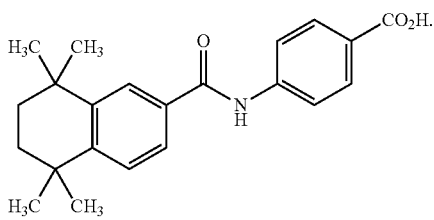

(also referred to herein as AM-580)

In another most preferred embodiment, the compound has the structure:

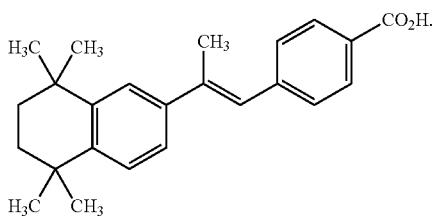

(also referred to herein as TTNPB)

The term "alkyl" refers to saturated non-aromatic hydrocarbon chains that may be a straight chain or branched chain, containing the indicated number of carbon atoms. Exemplary alkyls include, but are not limited to, methyl, propyl, butyl, pentyl, isobutyl and propargyl.

The term "alkenyl" refers to non-aromatic hydrocarbon chains that may be a straight chain or branched chain, comprising at least one double bond and containing the indicated number of carbon atoms.

The term "alkynyl" refers to non-aromatic hydrocarbon chains that may be a straight chain or branched chain, comprising at least one triple bond and containing the indicated number of carbon atoms.

The term "aryl" refers to a 6-carbon monocyclic or 10-carbon bicyclic aromatic ring system wherein 0, 1, 2, 3, or 4 atoms of each ring may be substituted by a substituent. Exemplary aryl groups include, but are not limited to phenyl, naphthyl and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, quinolinyl, indolyl, thiazolyl, and the like.

In other aspects, compounds useful for enhancing hematopoietic stem cell engraftment include e.g., 1,2-didecanoyl-glycerol (10:0), 11,12 Epoxyeicosatrienoic acid (11,12 EET), 1-hexadecyl-2arachidonoyl glycerol, carbazole, 9-cis-retinoic acid, anandamide, carbacyclin, clofibrate, carbamyl PAF (C-PAF), Prostaglandin B2,5-hydroxydecanoate, and 1,2-dioctanoyl-sn-glycerol (DOG), or derivatives thereof.

In one embodiment, the compound has the structure:

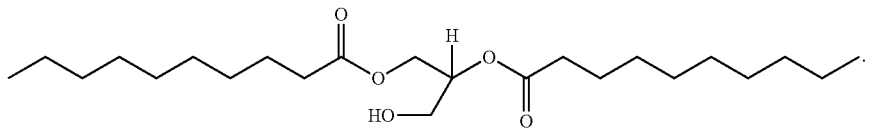

(1,2-didecanoyl-glycerol (10:0))

In another embodiment, the compound has the structure:

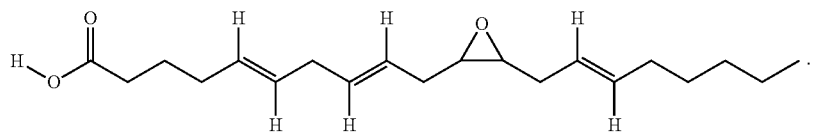

(11,12 Epoxyeicosatrienoic acid (11,12 EET))

In another embodiment, the compound has the structure:

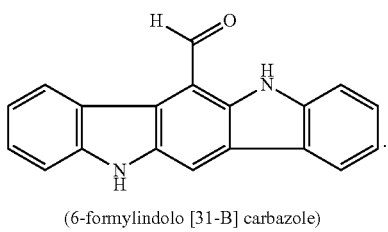 [SMILES: O=Cc1c2[nH]c3ccccc3c2cc2[nH]c3ccccc3c12]

(6-formylindolo [31-B] carbazole)

In another embodiment, the compound has the structure:

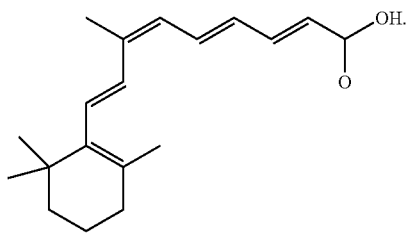

(9-cis-retinoic acid)

In another embodiment, the compound has the structure:

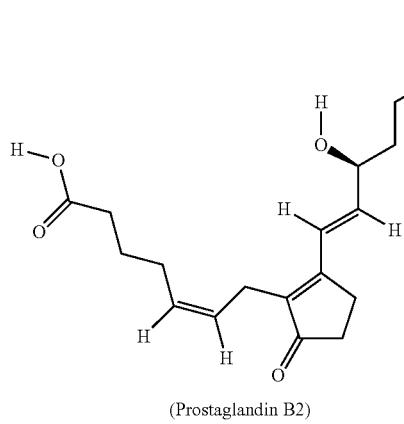

(Prostaglandin B2)

In another embodiment, the compound has the structure:

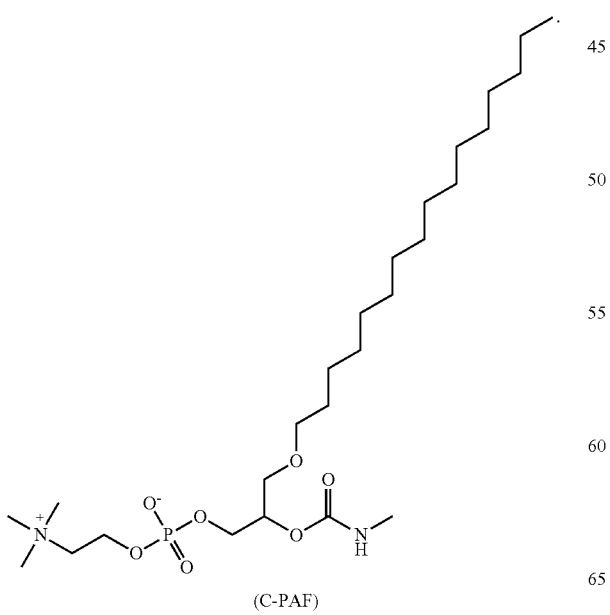

(C-PAF)

In another embodiment, the compound has the structure:

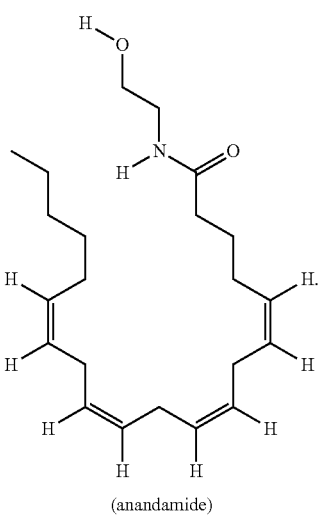

(anandamide)

In another embodiment, the compound has the structure:

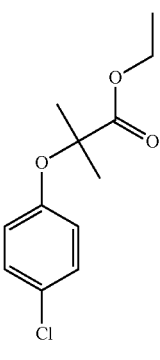

(carbacyclin)

In another embodiment, the compound has the structure.

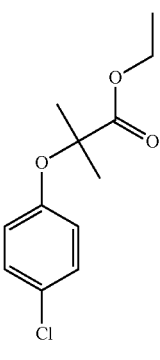

(clofibrate)

In another embodiment, the compound has the structure:

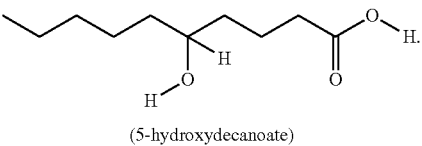

(5-hydroxydecanoate)

In another embodiment, the compound has the structure:

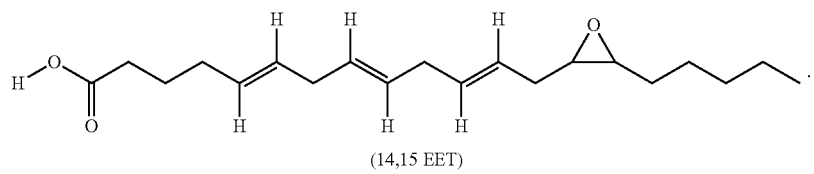 [SMILES: CCCCCC1OC1C/C=C/C/C=C/C/C=C/CCCC(=O)O]

(14,15 EET)

In another embodiment, the compound has the structure:

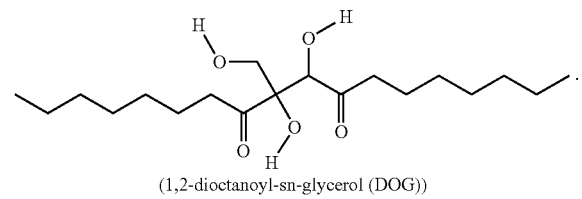 [SMILES: CCCCCCCC(=O)C(O)C(O)(CO)C(=O)CCCCCCC]

(1,2-dioctanoyl-sn-glycerol (DOG))

In one embodiment, two or more of the compounds described herein are administered together to promote hematopoietic stem cell engraftment. In another embodiment, at least one additional agent is used in combination with a compound as described above. In one embodiment, the additional agent is Prostaglandin E2. In other embodiments, the additional agent is 16-,16-dimethyl Prostaglandin E2 (dmPGE2) (available as FT1050 from FATE THERAPEUTICS™) or BIO. A combination of agents may be administered simultaneously or separately at an interval that permits enhanced hematopoietic stem cell engraftment. For example, an agent that enhances early engraftment (e.g., 0-2 weeks) may be combined with an additional agent that enhances longer term engraftment (e.g., <2 weeks). One of skill in the art can determine an appropriate combination and dosage regime for each agent to permit enhanced engraftment in an individual.

In one embodiment, the hematopoietic stem cells are provided in an admixture comprising at least one compound as described herein and the admixture is administered to the subject during the transplantation procedure.

Zebrafish Competitive Transplant Model

The development of the adult zebrafish whole kidney marrow competitive transplantation assay described herein provides an important method to quantify hematopoietic stem/progenitor cell engraftment capability after marrow transplant, an equivalent of murine bone marrow competition transplantation. The conventional zebrafish kidney marrow transplantation using single marrow from one donor has two drawbacks: First the readout of engraftment requires sacrificing the wild-type recipients for fluorescence activated cell sorting (FACS) analysis; Second, the big variances among recipients and transplantation procedures hamper the use of this assay for engraftment quantification. The novel adult zebrafish whole kidney marrow competitive transplantation assay overcomes these problems and allows direct visualization and quantification of homing and engraftment.

A transparent adult zebrafish, casper, was used as a transplantation recipient. Casper is a double homozygous pigment mutant for the nacre allele (devoid of melanocytes) and the roy allele (devoid of iridophores and reduced melanoyctyes), which allows direct visualization of GFP labeled hematopoietic stem cell homing and engraftment without killing the recipients. Two marrows are used: Tg(β-actin:GFP) and Red GloFish® respectively to compete with each other at varying ratios e.g., 1:4, which can generate robust competition between the two donors. In one embodiment, the red marrow is the competitor, as well as an internal control for the transplant. At different timepoints post-transplant, the recipients are anesthetized and two pictures for each recipient are taken by a fluorescence stereomicroscope with GFP/DsRed filters individually. Images are analyzed by software, such as ImageJ, which can quantify the GFP/DsRed fluorescence intensity. The relative engraftment efficiency of the manipulated green marrow is measured by the ratio of the GFP intensity over the DsRed intensity within the same kidney region after background subtraction (labeled as G/R). This quantitative approach generates results positively correlated with the FACS analysis results.

Using this assay, it was confirmed that in vitro incubation of the green marrow with 10 µM dimethyl-prostaglandin E2 (dmPGE2) or 0.5 µM 6-bromoindirubin-3'-oxime (BIO) at room temperature for 2-4 hours can increase engraftment by 4 weeks post transplant. Furthermore, the zebrafish competitive transplant assay can be used to screen libraries of compounds for those that will enhance engraftment. This chemical screen provides a significant advantage over cell culture-based screen (where in vivo analysis is not possible) and murine models (where large-scaled chemical screens are not feasible).

Cell Transplantation

Transplantation of hematopoietic cells has become the treatment of choice for a variety of inherited or malignant diseases. While early transplantation procedures utilized the entire bone marrow (BM) population, recently, more defined populations, enriched for stem cells (CD34 cells) have been used. In addition to the marrow, such cells could be derived from other sources such as bone marrow stem cells mobilized to the peripheral blood (PB) and neonatal umbilical cord blood (CB).

The donor and the recipient can be a single individual or different individuals, for example, autologous or allogeneic transplants, respectively. When allogeneic transplantation is practiced, regimes for reducing implant rejection and/or graft vs. host disease, as well known in the art, should be undertaken. Such regimes are currently practiced in human therapy. The cell populations selected can also be depleted of T lymphocytes, which may be useful in the allogeneic and haploidentical transplants setting for reducing graft-versus-host disease.

Most advanced regimes are disclosed in publications by Slavin S. et al., e.g., J Clin Immunol 2002; 22:64, and J Hematother Stem Cell Res 2002; 11:265, Gur H. et al. Blood 2002; 99:4174, and Martelli M F et al, Semin Hematol 2002; 39:48, which are incorporated herein by reference.

In another embodiment of the invention, INPROL can be employed in a method for preparing autologous hematopoietic cells for transplantation, as described in U.S. Pat. No. 7,115,267, which is herein incorporated by reference in its entirety. The hematopoietic cells are treated ex vivo with an effective amount of INPROL to inhibit stem cell division and then purged of cancerous cells by administering to the marrow cultures an effective amount of a chemotherapeutic agent or radiation. Chemotherapy agents with specificity for cycling cells are preferred. Marrow thus treated is re-injected into the autologous donor. Optionally, the patient is treated with stem cell stimulatory amounts of INPROL and/or another agent known to stimulate hematopoiesis to improve the hematopoietic reconstitution of the patient. Such a technique allows for effective purging of tumor cells during autologous bone marrow grafts while protecting hematopoietic stem cells. Such protection can be afforded with either ex vivo or in vivo purging protocols. Once successfully transplanted, there is a need for stem cells to rapidly proliferate to regenerate normal bone marrow function. This can be afforded by the use of INPROL at stem cell stimulatory amounts which stimulates cycling of stem cells and enhances recovery of bone marrow function.

Methods for Administering Cells

Stem cells can be administered to a subject either locally or systemically. Methods for administering bone marrow transplants to a subject are known in the art and are described in medical textbooks, e.g., Whedon, M. B. (1991) Whedon, M. B. "Bone Marrow Transplantation: Principles, Practice, and Nursing Insights", Boston:Jones and Bartlett Publishers. In certain embodiments, bone marrow cells from a healthy patient can be removed, preserved, and then replicated and re-infused should the patient develop an illness which either destroys the bone marrow directly or whose treatment adversely affects the marrow. If the patient is receiving his or her own cells, this is called an autologous transplant; such a transplant has little likelihood of rejection.

Exemplary methods of administering stem cells to a subject, particularly a human subject, include injection or transplantation of the cells into target sites in the subject. The hematopoietic stem cells and/or hematopoietic progenitor cells can be inserted into a delivery device which facilitates introduction, by injection or transplantation, of the cells into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, or alternatively embedded in a support matrix when contained in such a delivery device.

Support matrices in which the stem cells can be incorporated or embedded include matrices which are recipient-compatible and which degrade into products which are not harmful to the recipient. The support matrices can be natural (e.g. collagen etc.) and/or synthetic biodegradable matrices. Synthetic biodegradable matrices include synthetic polymers such as polyanhydrides, polyorthoesters, and polylactic acid; see also, for example, U.S. Pat. No. 4,298,002 and U.S. Pat. No. 5,308,701.

As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is known in the art. The solution is preferably sterile and fluid to the extent that easy syringability exists.

Preferably, the solution is stable under the conditions of manufacture and storage and preserved against the contaminating action of microorganisms such as bacteria and fungi through the use of, for example, parabens, chlorobu-tanol, phenol, ascorbic acid, thimerosal, and the like. Solutions of the invention can be prepared by incorporating stem cells as described herein in a pharmaceutically acceptable carrier or diluent and, as required, other ingredients enumerated above, followed by filtered sterilization.

Dosage and Administration

In one aspect, the methods described herein provide a method for enhancing engraftment of hematopoietic stem and/or progenitor cells following a bone marrow transplant in a subject. In one embodiment, the subject can be a mammal. In another embodiment, the mammal can be a human, although the invention is effective with respect to all mammals. The method comprises administering to the subject an effective amount of a pharmaceutical composition comprising a compound of Formula (I) and/or a compound selected from the group consisting of: 1,2-didecanoyl-glycerol (10:0), 11,12 Epoxyeicosatrienoic acid (11,12 EET), 1-hexadecyl-2arachidonoyl glycerol, 6-formylindolo[3,2-B]carbazole, 9-cis-retinoic acid, anandamide, carbacyclin, clofibrate, carbamyl PAF (C-PAF), Prostaglandin B2,5-hydroxydecanoate, and 1,2-dioctanoyl-sn-glycerol (DOG) in a pharmaceutically acceptable carrier. The dosage range for the compound depends upon the potency, and are amounts large enough to produce the desired effect e.g., an increase in the efficiency and/or rate of hematopoietic progenitor cell or stem cell engraftment. The dosage should not be so large as to cause adverse side effects.

Generally, the dosage will vary with the particular compound used, and with the age, condition, and sex of the patient. The dosage can be determined by one of skill in the art and can also be adjusted by a physician in the event of any complication. Typically, the dose will range from 0.001 mg/kg body weight to 5 g/kg body weight. In some embodiments, the dose will range from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dose range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

A compound as described herein can be given once a day, less than once a day, multiple times a day, or continuously in order to achieve a therapeutically effective dose. Administration of the doses recited above can be repeated for a limited period of time. In a preferred embodiment, the doses recited above can be administered daily for several weeks or months. The duration of treatment depends upon the subject's clinical progress and responsiveness to therapy. A "therapeutically effective amount" is an amount of a compound that is sufficient to produce a measurable change in engraftment efficiency or rate (see "Efficacy Measurement" below). Such effective amounts can be gauged in clinical trials as well as animal studies.

Compounds useful with the methods described herein can be administered intravenously, intranasally, orally, by inhalation, intraperitoneally, intramuscularly, subcutaneously, intracavity, and can be delivered by peristaltic means, if desired, or by other means known by those skilled in the art. In one embodiment the compounds used herein are administered orally, or intravenously to a patient following hematopoietic progenitor cell transplantation. The compound can be administered intravenously by injection or by gradual infusion over time.

In some embodiments, a compound of Formula (I) and/or a compound selected from the group consisting of: 1,2-didecanoyl-glycerol (10:0), 11,12 Epoxyeicosatrienoic acid (11, 12 EET), 1-hexadecyl-2arachidonoyl glycerol, 6-formylindolo[3,2-B]carbazole, 9-cis-retinoic acid, anandamide, carbacyclin, clofibrate, carbamyl PAF (C-PAF), Prostaglandin B2,5-hydroxydecanoate, and 1,2-dioctanoyl-sn-glycerol (DOG) is administered as part of a combination therapy regime. Therapeutic compositions containing at least one compound as described herein can be conventionally administered in a unit dose form. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle. A combination of more than one agent can be administered in one or more pharmaceutical compositions (i.e., together in a unit dose, such as a pill or tablet, or as two separate compositions). In one embodiment, the agents are administered separately and can be administered in an order, or at an interval of time that provides effective hematopoietic stem cell graft enhancement as directed by one of skill in the art of medicine. In addition, the agents can be administered using the same or different modes of administration.

The compositions of a combination therapy are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of each active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Pharmaceutical Compositions

The present invention involves therapeutic compositions useful for practicing the therapeutic methods described herein. Therapeutic compositions contain a physiologically tolerable carrier together with an active compound as described herein, dissolved or dispersed therein as an active ingredient. In a preferred embodiment, the therapeutic composition is not immunogenic when administered to a mammal or human patient for therapeutic purposes, unless so desired.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the invention that will be effective in the treatment of a particular disorder or condition will depend on the nature of the disorder or condition, and can be determined by standard clinical techniques.

Efficacy Measurement

Assessing Engraftment

Engraftment after lethal ablation of the bone marrow can be assessed by measuring hematopoietic blood cell counts; in particular white blood cell counts. Following lethal ablation, recovery of normal white blood cell counts is a functional measure of successful engraftment. In a clinical context, this can be accompanied by the measurement of cellularity in the bone marrow through serial bone marrow punctions/biopsies and/or by human leukocyte antigen (HLA) typing of circulating white blood cells. Bone marrow aspirates can also be assessed for donor chimerism as a measure of engraftment.

All blood cell types can be indicative of engraftment, but depending on their half lives, provide a more or less sensitive measure of engraftment. Neutrophils have a very short half life (just hours in the blood), and thus are a very good measure of early engraftment. Platelets also have a short half life, but they are usually the last blood element to recover to pre-transplant levels, which may not make them suitable as a marker of early engraftment.

Thus, it is noted herein that cells useful for determining engraftment of hematopoietic progenitor cells are those that recover relatively rapidly following transplantation and have a relatively short half-life (e.g., neutrophils). In one embodiment of the methods described herein, hematopoietic progenitor cell engraftment is assessed by detecting and/or measuring the level of recovery of neutrophils in an individual.

Efficacy

The efficacy of a given treatment to enhance hematopoietic cell engraftment can be determined by the skilled clinician. However, a treatment is considered "effective treatment," as the term is used herein, if any one or all of the signs or symptoms of e.g., poor hematopoietic cell engraftment are altered in a beneficial manner, other clinically accepted symptoms are improved, or even ameliorated, e.g., by at least 10% following treatment with a compound as described herein. Efficacy can also be measured by a failure of an individual to worsen as assessed by hospitalization, need for medical interventions (i.e., progression of the disease is halted), or incidence of engraftment failure. Methods of measuring these indicators are known to those of skill in the art and/or are described herein. Treatment includes any treatment of a disease in an individual or an animal (some non-limiting examples include a human, or a mammal) and includes: (1) inhibiting the disease, e.g., preventing engraftment failure; or (2) relieving the disease, e.g., causing regression of symptoms. An effective amount for the treatment of a disease means that amount which, when administered to a mammal in need thereof, is sufficient to result in effective treatment as that term is defined herein, for that disease. Efficacy of an agent can be determined by assessing physical indicators of, for example hematopoietic cell engraftment, such as e.g., neutrophil production, white blood cell count, hematopoietic cell numbers, presence/absence of anemia etc. Efficacy can be assessed in animal models of bone marrow transplantation, for example treatment of a rodent following bone marrow transplantation, and any treatment or administration of the compositions or formulations that leads to an increase of at least one symptom of hematopoietic cell engraftment.

Kits

Also provided herein are kits comprising components for (a) ex vivo treatment of isolated hematopoietic stem cells, (b) preparing admixtures of isolated HSC and a compound as described herein, and (c) administration of a compound as described herein to a subject.

In one embodiment, provided herein is a pack or kit comprising one or more containers filled with one or more of the compounds described herein described herein in the 'Compounds' section. Thus, for example, a kit described herein comprises one or more compounds of Formula I. Such kits optionally comprise solutions and buffers as needed or desired. The kit optionally includes containers or compositions for making an expanded population of isolated HSC. Optionally associated with such pack(s) or kit(s) are instructions for use and packaging materials therefor. In one embodiment, the kit further comprises additional agent such as prostaglandin E2, 16-,16-dimethyl Prostaglandin E2 (dmPGE2) (available as FT1050 from FATE THERAPEUTICS™), and/or BIO.

Also provided is a kit for providing an effective amount of a compound as described herein to enhance engraftment by administering to a subject and comprising one or more doses of at least one compound as described herein for use over a period of time, wherein the total number of doses of the at least one compound in the kit equals the effective amount of the compound or combination thereof sufficient to enhance engraftment in a subject. The period of time is from about one to several days or weeks or months. Thus, the period of time is from at least about five, six, seven, eight, ten, twelve, fourteen, twenty, twenty-one or thirty days or more or any number of days between one and thirty. The doses of the at least one compound can be administered once, twice, three times or more daily or weekly. The kit provides one or multiple doses for a treatment regimen.

A kit for providing an effective amount of at least one compound as described herein for treating isolated HSCs is described. The kit comprises one or more aliquots of at least one compound or combinations thereof for administration to HSC or a mixture of HSC and HSC-supporting cells over a period of time, wherein the aliquots equal the effective amount of the compounds required to expand the population of HSC. The period of time is from about one to several hours or one to several days. The amount of the compound or combination thereof is administered once, twice, three times or more daily or weekly and the kit provides one or multiple aliquots.

Optionally, the methods and kits comprise effective amounts of at least one compound for administering to the subject to effect enhanced engraftment in a second or subsequent regime for a specific period of time. The second or subsequent period of time, like the first period of time, is, for example, at least one or more days, weeks or months, such as, for example, at least four, five, six, seven, eight, nine, ten, eleven, twelve, fourteen, twenty one, or thirty days or any number of days between. In the methods herein, the interval between the first treating period and the next treating period is optionally, for example, days, weeks, months or years. Thus, the interval between the first period of time and the next period of time is, for example, at least four, five, six, seven, eight, nine, ten, eleven, twelve, fourteen, twenty one, or twenty eight days or in number of days between. This treating schedule is repeated several times or many times as necessary. Such schedules are designed to correlate with repeated bone marrow depleting events such as repeated chemotherapy treatments or radiation therapy treatments. Optionally, a drug delivery device or component thereof for administration is included in a kit. Disclosed are materials or steps in a method, compositions, and components that are used for, are used in conjunction with, are used in preparation for, or are products of the disclosed method and compositions. These and other materials are disclosed herein, and it is understood that when combinations, subsets, interactions, groups, etc. of these materials or steps are disclosed that, while specific reference of each various individual and collective combinations and permutation of these materials or steps may not be explicitly disclosed, each is specifically contemplated and described herein.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. A method for enhancing hematopoietic cell engraftment in a subject, the method comprising:

(a) contacting a population of hematopoietic cells with a compound of Formula I

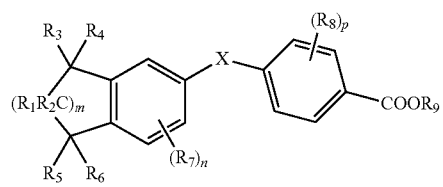

(I)

wherein X is selected from the group consisting of: O, S, SS, $NR_{10}$, C(O), OC(O), C(O)O, $NR_{10}$C(O), C(O)$NR_{10}$, C(S) $NR_{10}$, $NR_{10}$C(S), C(O)S, SC(O), SC($R_{10}$)$_2$, C($R_{10}$)$_2$S, optionally substituted $C_1$-$C_6$ alkyl, optionally substituted $C_2$-$C_6$ alkenyl, optionally substituted $C_2$-$C_6$ alkynyl, C(O)C ($R_{10}$)$_2$, C($R_{10}$)$_2$C(O), OC($R_{10}$)$_2$, C($R_{10}$)$_2$O, $NR_{10}$C($R_{10}$)$_2$, C($R_{10}$)$_2$$NR_{10}$, $CR_{10}$=$CR_{10}$, C(O)$CR_{10}$=$CR_{10}$, $CR_{10}$=$CR_{10}$C(O), C($R_{10}$)=N, N=C($R_{10}$), N=N, $N^+(O^-)$=N, N=$N^+(O^-)$ and

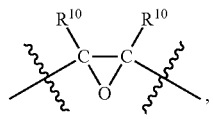

wherein $R_1$, $R_2$, $R_3$, $R_4$, $R_5$ and $R_6$ are independently for each occurrence hydrogen or optionally substituted $C_1$-$C_6$ alkyl, optionally substituted $C_2$-$C_6$ alkenyl, optionally substituted $C_2$-$C_6$ alkynyl, aryl or heteroaryl, wherein $R_7$ and $R_8$ are independently for each occurrence halogen, hydroxyl, SH, optionally substituted $C_1$-$C_6$ alkyl, optionally substituted $C_1$-$C_{10}$ alkoxy, optionally substituted $C_1$-$C_6$ alkylthio, nitro or cyano; and (b) administering treated cells from step (a) to a subject in need thereof, wherein the engraftment of the hematopoietic cells treated with the compound is increased compared to engraftment of a population of untreated hematopoietic cells.

2. The method of paragraph 1, wherein the compound has a structure of

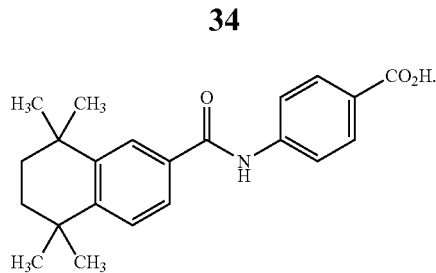

3. The method of paragraph 1 or 2, wherein the compound has a structure of

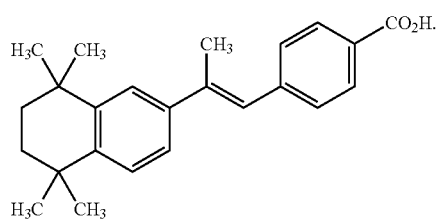 [SMILES: C/C(=C\c1ccc(C(=O)O)cc1)c1ccc2c(c1)C(C)(C)CCC2(C)C]

4. The method of any one of the preceding paragraphs, wherein the population of hematopoietic cells is derived from cord blood.

5. The method of any one of the preceding paragraphs, wherein the population of hematopoietic cells is derived from bone marrow.

6. The method of any one of the preceding paragraphs, wherein the population of hematopoietic cells is derived from blood.

7. The method of any one of the preceding paragraphs, wherein the population of hematopoietic cells are isolated cells.

8. The method of any one of the preceding paragraphs, wherein the population of hematopoietic cells is a heterogeneous or homogeneous population of cells.

9. The method of any one of the preceding paragraphs, wherein the contacting step is performed on ex vivo cells in culture.

10. The method of any one of the preceding paragraphs, wherein the subject is a human subject.

11. The method of any one of the preceding paragraphs, wherein the hematopoietic cells are hematopoietic stem cells.

12. The method of any one of the preceding paragraphs, wherein the hematopoietic cells are hematopoietic progenitor cells.

13. A method for enhancing hematopoietic cell engraftment in a subject following hematopoietic cell transplantation, the method comprising: administering to a subject following hematopoietic cell transplantation a therapeutically effective amount of a compound of Formula I (I)

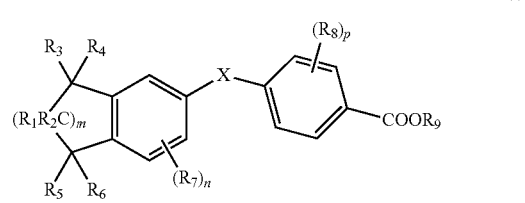

wherein X is selected from the group consisting of: O, S, SS, $NR_{10}$, C(O), OC(O), C(O)O, $NR_{10}$C(O), C(O)$NR_{10}$, C(S) $NR_{10}$, $NR_{10}$C(S), C(O)S, SC(O), SC($R_{10}$)$_2$, C($R_{10}$)$_2$S, optionally substituted $C_1$-$C_6$ alkyl, optionally substituted $C_2$-$C_6$ alkenyl, optionally substituted $C_2$-$C_6$ alkynyl, C(O)C ($R_{10}$)$_2$, C($R_{10}$)$_2$C(O), OC($R_{10}$)$_2$, C($R_{10}$)$_2$O, $NR_{10}$C($R_{10}$)$_2$, C($R_{10}$)$_2$$NR_{10}$, $CR_{10}$=$CR_{10}$, C(O)$CR_{10}$=$CR_{10}$, $CR_{10}$=$CR_{10}$C(O), C($R_{10}$)=N, N=C($R_{10}$), N=N, $N^+(O^-)$=N, N=$N^+(O^-)$ and

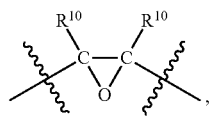

wherein $R_1$, $R_2$, $R_3$, $R_4$, $R_5$ and $R_6$ are independently for each occurrence hydrogen or optionally substituted $C_1$-$C_6$ alkyl, optionally substituted $C_2$-$C_6$ alkenyl, optionally substituted $C_2$-$C_6$ alkynyl, aryl or heteroaryl, wherein $R_7$ and $R_8$ are independently for each occurrence halogen, hydroxyl, SH, optionally substituted $C_1$-$C_6$ alkyl, optionally substituted $C_1$-$C_{10}$ alkoxy, optionally substituted $C_1$-$C_6$ alkylthio, nitro or cyano; and wherein the level of engraftment of the hematopoietic cells in the subject treated with the compound is increased compared to engraftment of a population of hematopoietic cells in an untreated subject.

14. The method of paragraph 13, wherein the compound has a structure of

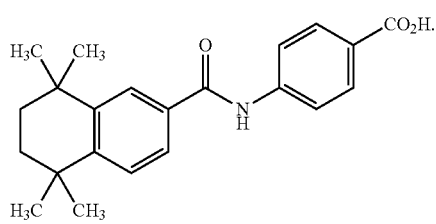

15. The method of paragraph 13 or 14, wherein the compound has a structure of

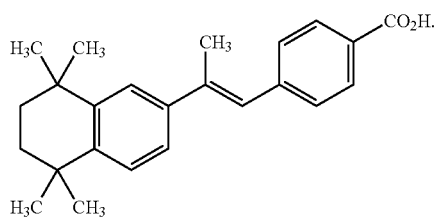

16. The method of any one of paragraphs 13-15, wherein the population of hematopoietic cells is derived from cord blood.
17. The method of any one of paragraphs 13-16, wherein the population of hematopoietic cells is derived from bone marrow.
18. The method of any one of paragraphs 13-17, wherein the population of hematopoietic cells is derived from blood.
19. The method of any one of paragraphs 13-18, wherein the population of hematopoietic cells are isolated cells.
20. The method of any one of paragraphs 13-19, wherein the population of hematopoietic cells is a heterogeneous or homogeneous population of cells.
21. The method of any one of paragraphs 13-20, wherein the subject is a human subject.
22. The method of any one of paragraphs 13-21, wherein the hematopoietic cells are hematopoietic stem cells.
23. The method of any one of paragraphs 13-22, wherein the hematopoietic cells are hematopoietic progenitor cells.
24. A method for enhancing hematopoietic cell engraftment in a subject, the method comprising:
   (a) contacting a population of hematopoietic cells with a compound selected from the group consisting of: 1,2-didecanoyl-glycerol (10:0), 11,12 Epoxyeicosatrienoic acid (11, 12 EET), 1-hexadecyl-2arachidonoyl glycerol, 6-formylindolo[3,2-B]carbazole, 9-cis-retinoic acid, anandamide, carbacyclin, clofibrate, carbamyl PAF (C-PAF), Prostaglandin B2,5-hydroxydecanoate, and 1,2-dioctanoyl-sn-glycerol (DOG); and
   (b) administering treated cells from step (a) to a subject in need thereof,
   wherein the engraftment of the hematopoietic cells treated with the compound is increased compared to engraftment of a population of untreated hematopoietic cells.
25. The method of any one of the preceding paragraphs, further comprising administering at least one additional agent that enhances hematopoietic stem cell engraftment.
26. The method of any one of the preceding paragraphs, wherein the at least one additional agent is PGE2 or BIO.

EXAMPLES

Example 1

Zebrafish Competitive Transplant Assay Development

Described herein is an adult zebrafish competitive marrow transplantation assay, which can be used to directly visualize and quantify engraftment, and measure the migration, self-renewal, proliferation and differentiation properties of hematopoietic stem cells (HSCs) in zebrafish. A chemical screen with the zebrafish WKM competitive transplantation model accelerates the discovery of novel pathways and signaling networks regulating these properties of HSCs. The zebrafish embryonic and adult hematopoietic models also help to characterize and understand the mechanism of the pathways. Last but not least, compared with traditional genetic methods, chemical genetic approaches provide not only pathways relevant to the biological process, but also small molecules as the starting point of drug development to increase the HSC engraftment capability and improve the engraftment efficiency of human HSC transplantation.

A double-color labeled competitive transplantation assay was developed, as shown by the flow chart in FIG. 1A. GFP+ and DsRed2+ marrow cells are isolated from Tg(β-actin: GFP) and commercially available Red GloFish®. The two donor populations are mixed at a certain ratio and injected into sublethally irradiated casper recipients retro-orbitally. The DsRed2+ marrow is used as the competitor. Four weeks later, the engraftment is visualized by fluorescence dissection scope. Pictures of GFP and DsRed engraftment are taken for each recipient and analyzed by ImageJ. The kidney region is manually selected and the average fluorescence intensities of both green and red are measured within the same region. The average background intensity is measured in a region outside the fish, and subtracted from the kidney intensity. The calculation of the relative engraftment is shown by the equation in FIG. 1B.

Figure 2:
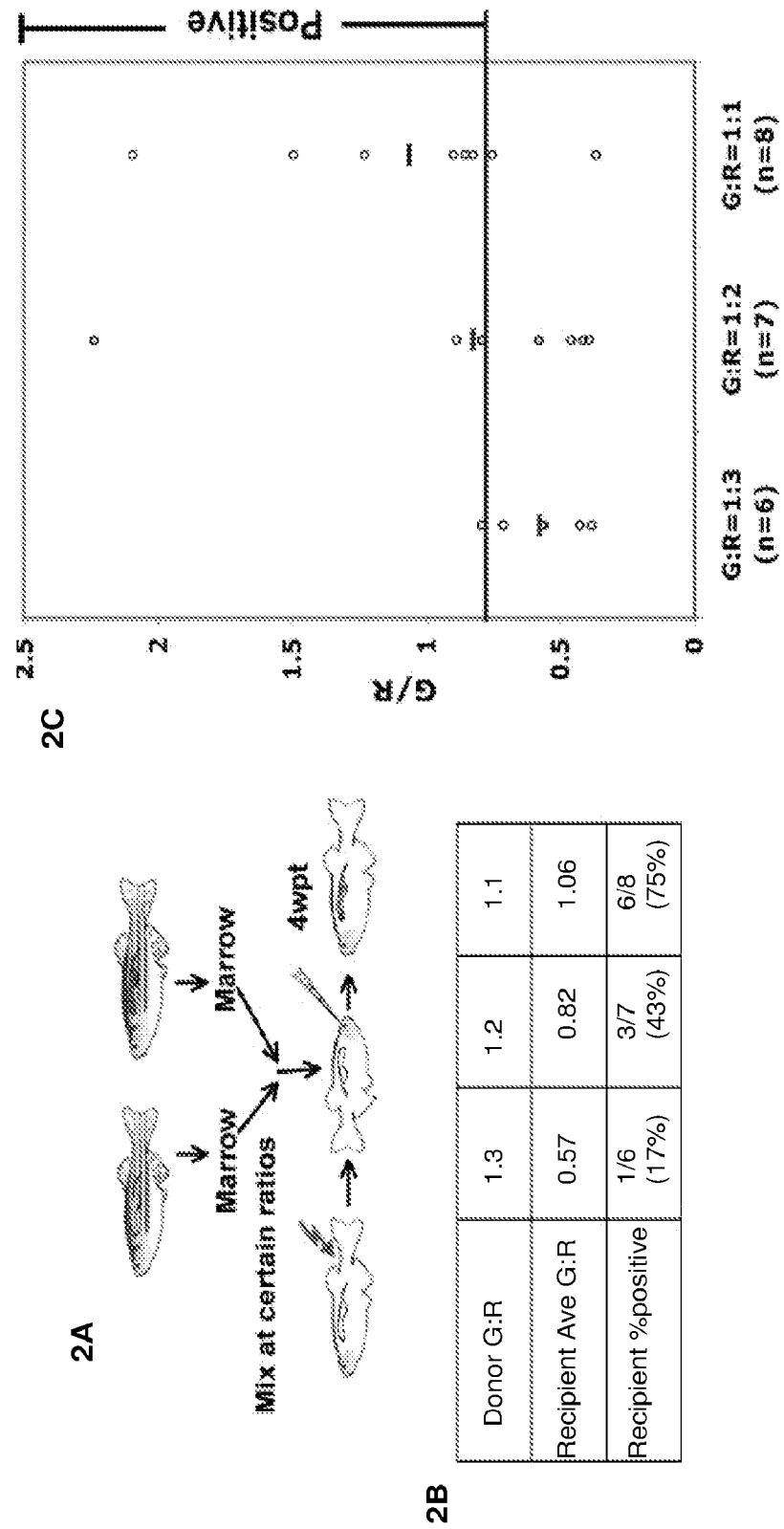
FIGS. 2A-2C show data from a competitive transplantation assay that faithfully represents the donor ratio. 2A) is a schematic depicting the competitive transplant protocol. 2B) is a table indicating an increase in the green:red fluorescence ratio with increasing numbers of treated donor cells. 2C) is a graph depicting the data from FIG. 2B.

To test whether the competitive transplantation assay can faithfully and sensitively detect changes of the donor cell ratios, the donor G:R (green:red) ratios were increased from 1:3 to 1:2 to 1:1, while keeping the total number of donor cells constant as 200,000. The readout at 4 wpt (week post transplant) shows an increased G/R by increasing the donor G:R ratio (FIG. 2). The 1:3 group was set as the control, and its average G/R plus two standard deviation as the cutoff line. Recipients with a G/R above this line are called positive, which means their green marrows have a competitive advantage than the control. By increasing the donor G:R ratio, the percentage of positive recipients also increased as shown in the table in FIG. 2B. This result proves the assay can faithfully represent the donor ratio and sensitively detect the ratio changes.

Figure 3:
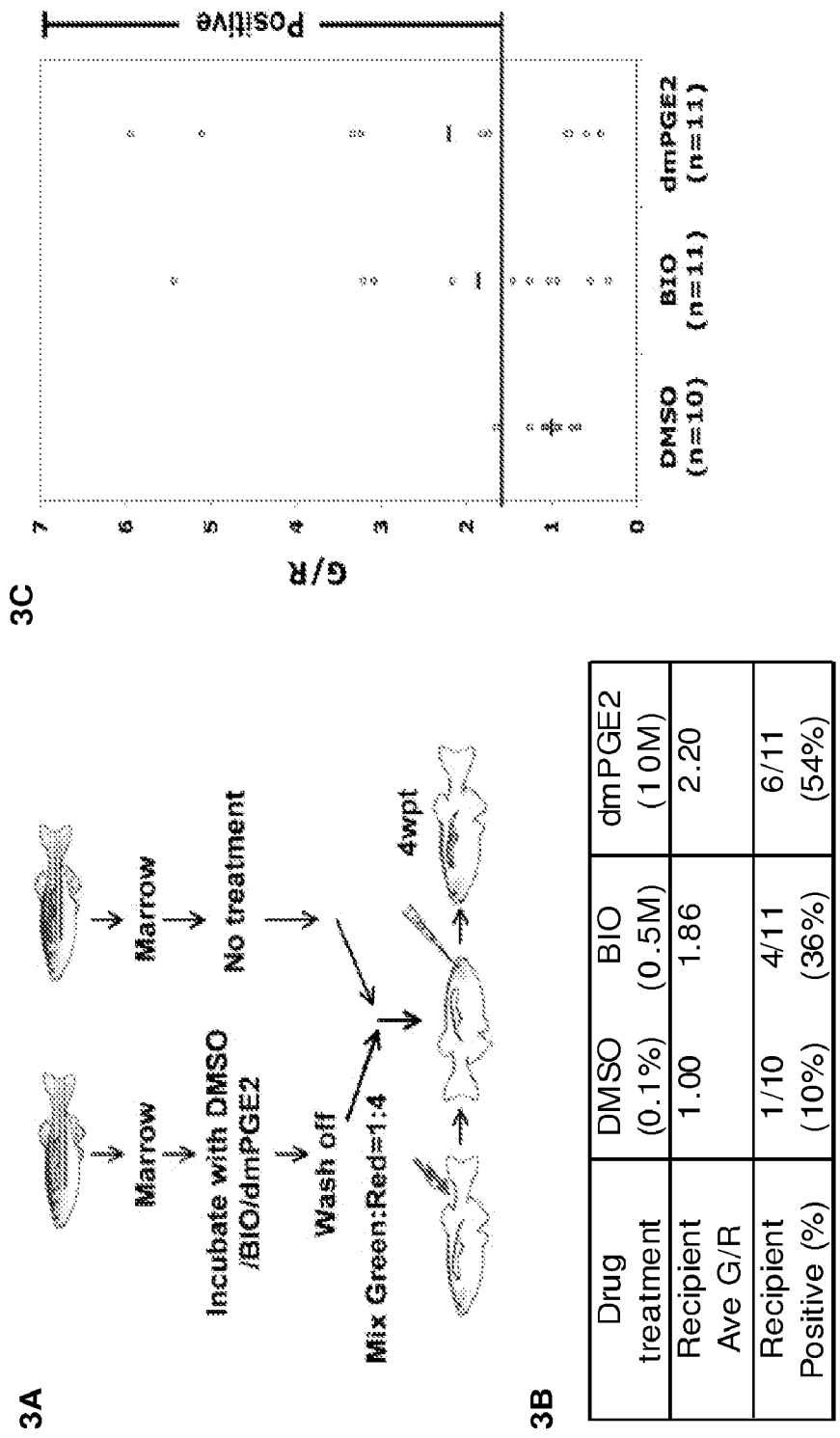
FIGS. 3A-3C shows the effect of positive control drugs on engraftment in the competitive transplantation assay. 3A) is a schematic of a protocol for a competitive transplant assay using drug treated cells. 3B) is a table representing fluorescence data from zebrafish transplanted with vehicle treated (DMSO) or drug treated cells. 3C) is a graph depicting the data from FIG. 3B.

The applicability of the zebrafish model was confirmed by testing two known signaling pathways regulating HSCs using a chemical genetic approach. Two compounds: BIO and dmPGE2 were chosen. BIO is a GSK-3 inhibitor and thus activates the Wnt pathway. dmPGE2 is a stabilized derivative of prostaglandin E2, which binds to the PGE2 receptor. Both pathways increase HSC self-renewal. After cell preparation, the green marrow cells were incubated with DMSO, BIO or dmPGE2 in vitro for 4 hrs, mixed with freshly isolated red marrow cells at a ratio of 1:4 and injected into casper. At 4 wpt, both the average G/R and the percentage of positive recipients in the BIO/dmPGE2 treated groups were significantly increased compared with a DMSO control (FIG. 3C). The results are very similar to what has been observed in mouse competitive transplant.

To explore the feasibility of using this competitive transplantation assay for a chemical screen, as well as the optimal timepoint for readout, small-scaled pilot screen was performed with 10 bioactive compounds. We started with 10 recipients per treatment, and followed the engraftment every week from 2 weeks post-transplant (wpt) to 4 wpt. The engraftment signal was not strong enough to observe the effect of most chemical treatments at 2 wpt (data not shown). By four weeks, dmPGE2 and BIO have an enhanced signal above the rest of the chemicals tested. This indicates that although stem cell homing, lodgement, and engraftment have taken place by 2 weeks, the amplification of hematopoiesis between 2-4 weeks allows a more sensitive detection of the success of enhancement of these biological processes, particularly for a screen. In later timepoints, recipient survival dropped sharply due to multiple reasons. In one embodiment, the 4 wpt is the optimal timepoint for the screen.

An Exemplary Competitive Transplantation Protocol.

Adult zebrafish donors are anaesthetized with 0.2% tricaine before blood and kidney collection. Peripheral blood is obtained from adult casper by cardiac puncture with micropipette tips coated with heparin and collected into 0.9×PBS containing 5% FCS. About 3-5 million red blood cells are harvested from one donor. To dissect whole kidney marrow (WKM), a ventral midline incision is made on the donor fish. Whole kidney is dissected out and placed into ice-cold 0.9× PBS containing 5% FCS. Single-cell suspensions are generated by aspiration followed by filtering through a 40-m nylon mesh filter into a 50 ml conical tube. The flow-though part is diluted with a final volume of 25 ml and centrifuged at 1,500 rpm for 8 minutes. The supernatant is discarded and the pellet cells are resuspended in 1 ml 0.9×PBS containing 5% FCS. The number of viable cells are counted with a hemocytometer. On average, 500,000-700,000 cells can be harvested per donor. Finally, the peripheral blood and kidney marrow cells are centrifuged at 1,500 rpm for 8 minutes, resuspended in 0.9×PBS containing 5% FCS and mixed at a certain ratio and concentration. Casper recipients are anesthetized in tricaine. 4 μl of the cell suspension mixture described above is injected into the circulation retro-orbitally through a Hamilton syringe (26 s gauge, 10 μl volume). The retro-orbital injection is much more consistent than the intra-cardiac injection previously used. Transplanted recipients can be anesthetized in tricaine and visualized over time on a Zeiss Discovery V8 stereomicroscope with a 1.2× PlanApo lens and GFP/DsRed filters. Images are captured using AxioVision software and for each recipient, two images are taken with GFP or DsRed filter respectively. The images are all saved in .tif format and analyzed using ImageJ software. Kidney region is manually selected for every fish and the average fluorescence intensities per pixel of both GFP and DsRed are measured within the same region. Background for each image is measured in a region outside the fish, and subtracted from the correlated kidney fluorescence intensity. The relative engraftment efficiency (G/R) for every single recipient is measured by the ratio of GFP intensity (background subtracted) and DsRed intensity (background subtracted).

One of the advantages of the casper fish is that the kidney can be visualized as a solid organ. This establishes a stem cell niche based on localized fluorescence intensity. The ratio of green to red marrow cells is well correlated between the ImageJ fluorescence intensity and FACS analysis. As a screening technology, fluorescence intensity in the kidney has great advantages since the animal does not have to be sacrificed for FACS analysis and can be followed longitudinally. In addition, the green to red intensity is positively correlated to the FACS results. Even visual examination of green vs. red under a fluorescent dissecting scope reveals competitive engraftment.

Figure 4:
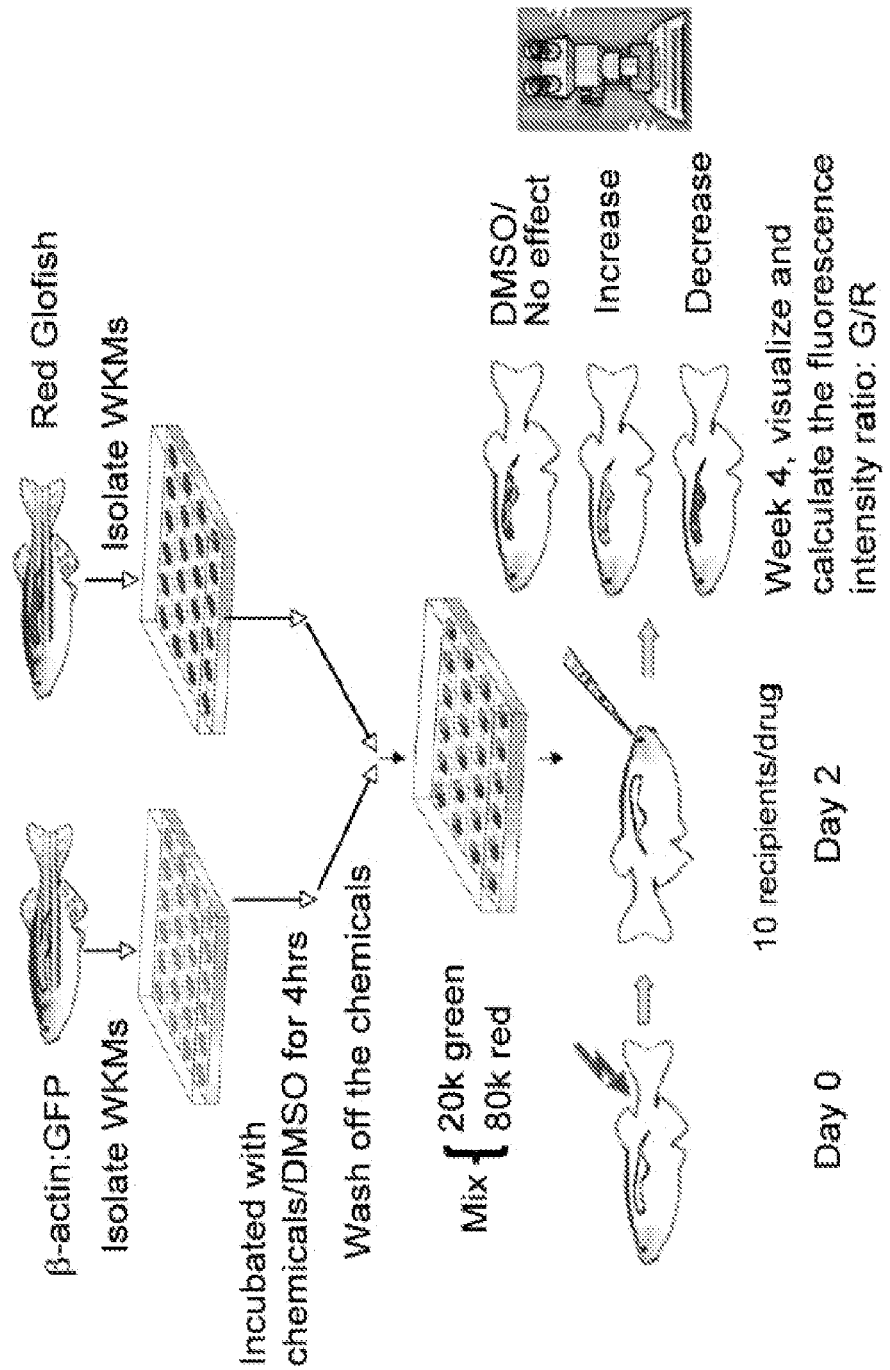
FIG. 4 is a schematic flow chart depicting a chemical screen using the adult zebrafish competitive marrow transplantation assay.
Figure 5:
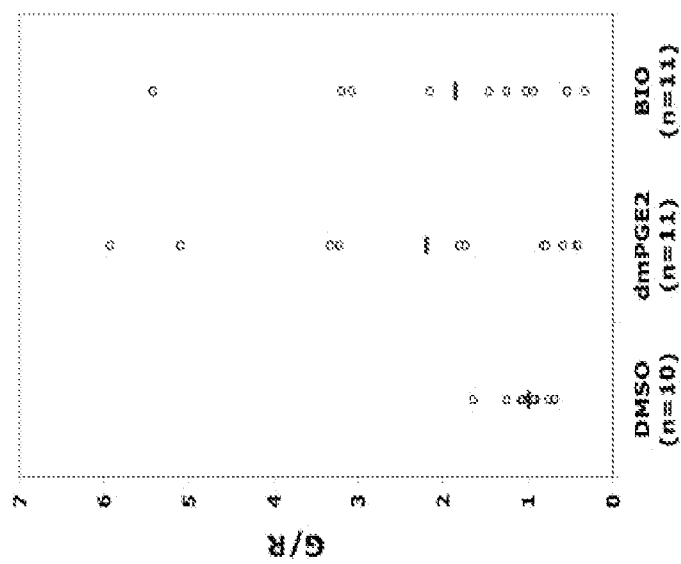
FIG. 5 is a graph showing competitive transplantation with different drug treatments for the GFP+ marrow.

With the competitive transplant assay established, it was evaluated whether chemicals of known biologic action in stem cells could affect engraftment in zebrafish. An experimental approach for the competitive transplant assay is outlined herein in FIG. 4. A variety of different times from 2 weeks to 3 months after transplantation were studied. The 4-week time period is more amenable to high-throughput screens than waiting the 3 months for long-term reconstitution. Although the fish can be evaluated at 3 months, for screening purposes a chemical that would allow enhanced engraftment at 4 weeks and also at 3 months is preferred. One such chemical is dmPGE2, which enhances hematopoietic self-renewal in mouse, and BIO, a chemical that inhibits GSK-3, leads to enhancement of the wnt pathway and also increases self-renewal. Both of these chemicals score positive in the competitive transplant model in the zebrafish at 4 weeks and at 3 months.

The Chemical Screen.

The chemical screen utilizes β-actin GFP whole kidney marrow competed against red glow fish whole kidney marrow. 20,000 GFP positive cells are competed against 80,000 DsRed positive marrow cells. In this test:competitor ratio, low levels of GFP expressing marrow at 4 weeks is evident. The cells are incubated in the chemicals for 4 hours before transplantation and washed off 10 recipients are injected with the treated cells at day 2 after the irradiation and by 4 weeks, the recipient casper fish is visualized and the fluorescence intensity ratio of green vs. red is calculated. Recipients in which an increased intensity with the green compared to red is observed indicates a chemical that enhances engraftment, perhaps by affecting homing, engraftment, or self-renewal.

β-actin:GFP (whole kidney marrow) WKM cells are resuspended in 0.9XPBS containing 5% FCS at a concentration of 1,000/1 and aliquoted into a 96-well sterilized clear round-bottom tissue culture plate (200 μl/well). Compounds from ICCB Known Bioactive Library are added into each well (1:200 dilution), and the cells are incubated with compounds at room temperature for 4 hrs before being centrifuged at 1,500 rpm for 8 minutes. 800 k WKM cells from Red GloFish and 1,600 k peripheral blood cells are added into each well to make the final volume in each well to be 40 l. The cells in each well are transplanted into 10 recipients. The relative engraftment efficiency is evaluated at 4 week post transplant.

Figure 6:
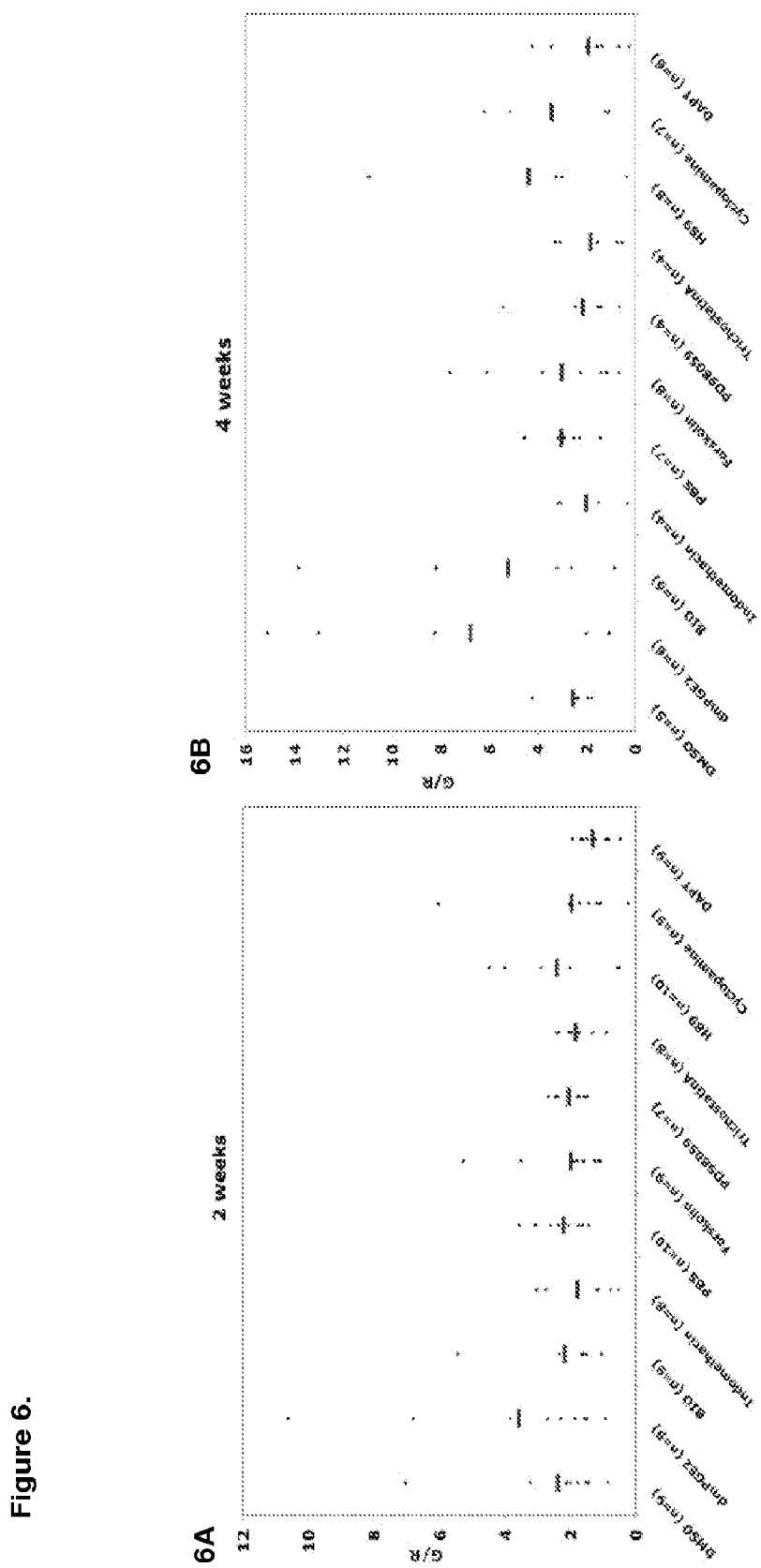
FIGS. 6A and 6B are each a graph that shows fluorescence data for transplanted zebrafish with cells treated with compounds from an exemplary chemical screen at both 2 wpt (6A) and 4 wpt (6B).

Initially, a small pilot screen using a panel of ten bioactive chemicals was screened and confirmed the optimal time for evaluation (FIG. 6). Two weeks after the transplant, there was very little engraftment observable based treatment with chemicals. By four weeks, dmPGE2 and BIO have an enhanced signal above the rest of the chemicals tested.

The throughput that can be accomplished is one screen per day and testing 20 chemicals per day. This would mean that 10 recipient fish are used for each chemical assayed and these fish will be followed for 2.5 to 3 months. To do the screen, 12 green fish and 45 red fish would be needed as donors and these should be old enough and of sufficient size to provide sufficient marrow cells for the screen. In terms of an experimental day, 1.5 hours of time is needed for GFP positive marrow preparation and then the cells are treated with chemicals for 4 hours. Then red marrow preparation is done for another 1.5 hours and about 1.5 hours is required for transplantation of 220 fish. This library consists of 500 chemicals that have been selected for their known biological activity.

Example 2

Exemplary Compounds that Enhance Engraftment 240 compounds have been screened using the Zebrafish competitive transplant assay described herein above. Twenty compounds showed a positive effect on engraftment in the primary screen. Ten out the twenty compounds have been repeated in the second round of the screen. Compounds having the following structures have a positive effect on hematopoietic stem and/or progenitor cell engraftment as shown in Table 1:

TABLE 1

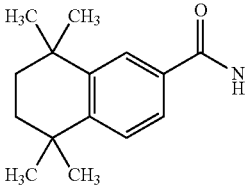

AM-580

TTNPB

Compounds of Formula (I) enhance engraftment in a zebrafish model

| compound name | conc. | mechanism | P value |
| --- | --- | --- | --- |
| AM-580 | 5 mM | Nuclear receptor ligands Retinoid RAR agonist | 0.1039 |
| TTNPB | 5 mM | Nuclear receptor ligands Retinoid RAR agonist | 0.10 |

Exemplary compounds that enhance engraftment in a zebrafish model

| compound name | conc. | mechanism | P value |
| --- | --- | --- | --- |
| 1,2-Didecanoyl-glycerol (10:0) (DAG) | 5 mM | Bioactive lipids Activates PKC | 0.0279 |
| 11,12-Epoxyeicosatrienoic acid (11,12-EET) | 0.5 mM | Bioactive lipids Bioactive arachidonic acid metabolite | 0.0383 |
| C-PAF | 5 mM | Bioactive lipids PAF receptor agonist | 0.0267 |
| Prostaglandin E2 (PGE2) | 5 mM | Bioactive lipids Prostaglandin EP receptor agonist | 0.06 |
| 1,2-Dioctanoyl-sn-glycerol (DOG) | 5 mM | Bioactive lipids Activates PKC | 0.10 |
| 14,15-Epoxyeicosatrienoic acid (14,15-EET) | 0.5 mM | Bioactive lipids Bioactive arachidonic acid metabolite | 0.088 |

Figure 7:
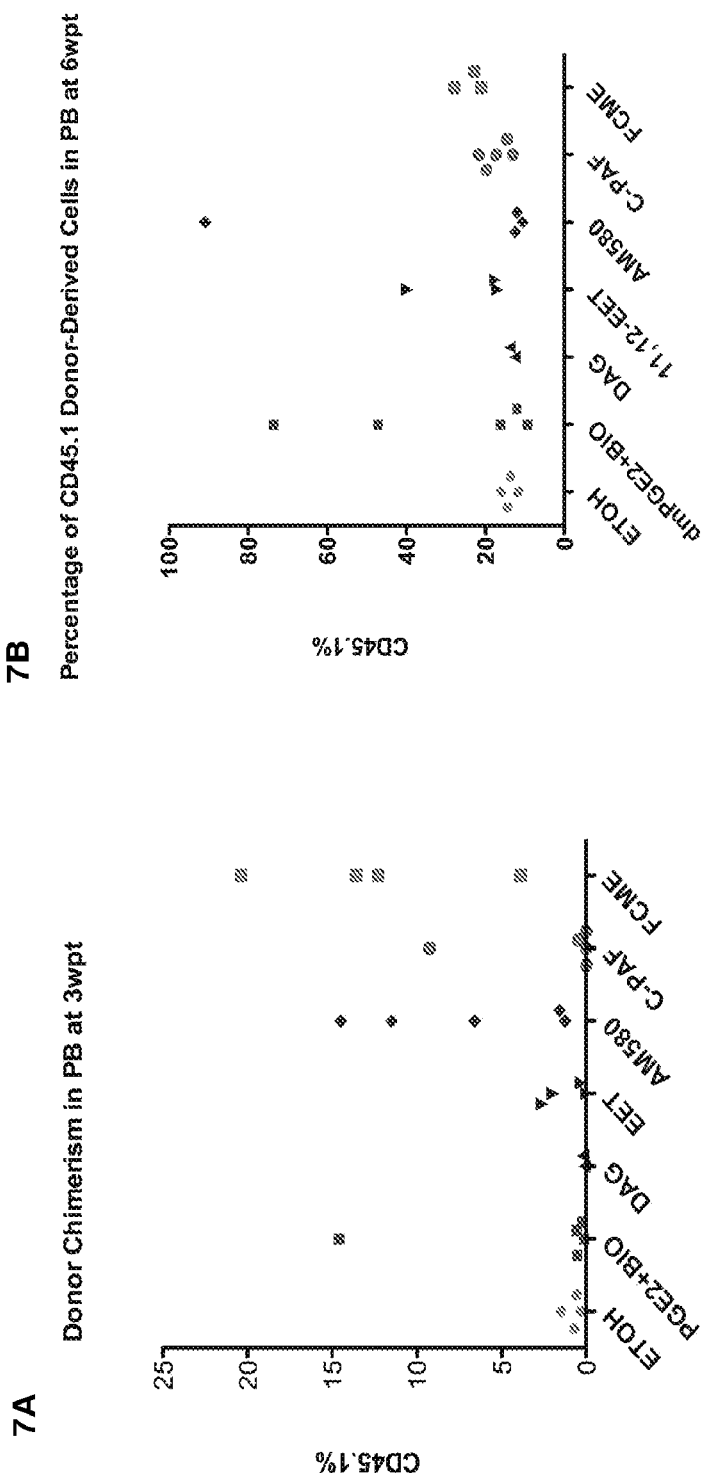
FIGS. 7A and 7B are each a bar graph depicting data representing a mouse competitive transplant assay that is used to confirm the accuracy of the zebrafish assay described herein.

Five positive compounds from the Zebrafish screen were further confirmed using a mouse whole bone marrow competitive transplantation assay. 20,000 CD45.1 donor bone marrow cells treated with different compounds at 37° C. for 3 hours, to compete with 200,000 CD45.2 bone marrow cells. The peripheral blood from each recipient are collected at different time points: 3 weeks post transplant (wpt), 6 wpt, and 12 wpt. The lineage contribution from CD45.1 donor marrows are analyzed by FACS. The 3 wpt and 6 wpt results are shown herein in FIG. 7. This experiment confirmed the drug effects of increasing marrow repopulation in mammals.

TABLE 2

A compound of Formula (I) enhances engraftment in a mouse model

| compound name | conc. | mechanism | Pvalue |
| --- | --- | --- | --- |
| AM-580 | 5 mM | Nuclear receptor ligands Retinoid RAR agonist | 0.1039 |

TABLE 3

Compounds that enhance hematopoietic cell engraftment in a mouse model.

| compound name | conc. | mechanism | Pvalue |
|---|---|---|---|
| 1,2-Didecanoyl-glycerol (10:0) | 5 mM | Bioactive lipids Activates PKC | 0.0279 |
| 11,12-Epoxyeicosatrienoic acid | 0.5 mM | Bioactive lipids Bioactive arachidonic acid metabolite | 0.0383 |
| AM-580 | 5 mM | Nuclear receptor ligands Retinoid RAR agonist | 0.1039 |
| C-PAF | 5 mM | Bioactive lipids PAF receptor agonist | 0.0267 |

The invention claimed is:

1. A method for enhancing hematopoietic cell engraftment in a subject, the method comprising:
    (a) contacting a population of hematopoietic cells with a compound having the structure of

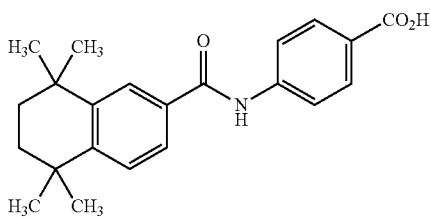 [SMILES: CC1(C)CCC(C)(C)c2cc(C(=O)Nc3ccc(C(=O)O)cc3)ccc21]

and;
    (b) administering treated cells from step (a) to a subject in need thereof,
    wherein the engraftment of said hematopoietic cells treated with said compound is increased compared to engraftment of a population of untreated hematopoietic cells.

2. The method of claim 1, wherein said population of hematopoietic cells is derived from cord blood.

3. The method of claim 1, wherein said population of hematopoietic cells is derived from bone marrow.

4. The method of claim 1, wherein said population of hematopoietic cells is derived from blood.

5. The method of claim 1, wherein said population of hematopoietic cells are isolated cells.

6. The method of claim 1, wherein said population of hematopoietic cells is a heterogeneous population of cells.

7. The method of claim 1, wherein said contacting step is performed on ex vivo cells in culture.

8. The method of claim 1, wherein said subject is a human subject.

9. The method of claim 1, wherein said hematopoietic cells are hematopoietic stem cells.

10. The method of claim 1, wherein said hematopoietic cells are hematopoietic progenitor cells.

11. The method of claim 1, wherein said population of hematopoietic cells is a homogeneous population of cells.

* * * * *